(12) United States Patent
Ware et al.

(10) Patent No.: US 9,982,023 B2
(45) Date of Patent: May 29, 2018

(54) COMPOSITIONS AND METHODS FOR TREATING AUTOIMMUNE AND INFLAMMATORY DISORDERS

(71) Applicant: SANFORD-BURNHAM MEDICAL RESEARCH INSTITUTE, San Diego, CA (US)

(72) Inventors: Carl F. Ware, La Jolla, CA (US); John Sedy, La Jolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days. days.

(21) Appl. No.: 13/677,703

(22) Filed: Nov. 15, 2012

(65) Prior Publication Data

US 2013/0164306 A1 Jun. 27, 2013

Related U.S. Application Data

(60) Provisional application No. 61/597,634, filed on Feb. 10, 2012, provisional application No. 61/560,081, filed on Nov. 15, 2011.

(51) Int. Cl.
| | |
|---|---|
| *C07K 14/03* | (2006.01) |
| *C07K 14/05* | (2006.01) |
| *C07K 16/28* | (2006.01) |
| *A61K 38/00* | (2006.01) |
| *C07K 14/705* | (2006.01) |

(52) U.S. Cl.
CPC ........ *C07K 14/03* (2013.01); *C07K 14/70578* (2013.01); *C07K 16/28* (2013.01); *A61K 38/00* (2013.01); *C07K 2319/00* (2013.01)

(58) Field of Classification Search
CPC ............ C07K 2317/76; C07K 2319/00; C07K 14/005; C07K 14/03; A61K 38/00; A61K 2039/505; A61K 38/177; C12N 2710/16622
See application file for complete search history.

(56) References Cited

U.S. PATENT DOCUMENTS

| | | | |
|---|---|---|---|
| 7,427,492 B1 | 9/2008 | Ni et al. | |
| 2009/0317401 A1* | 12/2009 | Bensussan et al. ........ | 424/144.1 |
| 2010/0129389 A1* | 5/2010 | Ware et al. ................ | 424/185.1 |
| 2010/0233758 A1* | 9/2010 | Kwon et al. ................ | 435/69.1 |
| 2011/0123551 A1* | 5/2011 | Ware et al. ................ | 424/172.1 |
| 2011/0171242 A1* | 7/2011 | Ware .......................... | 424/173.1 |
| 2011/0230647 A1* | 9/2011 | Murphy et al. ............ | 530/387.9 |
| 2012/0076798 A1* | 3/2012 | Granger et al. ........... | 424/158.1 |

FOREIGN PATENT DOCUMENTS

WO WO 2006/063067 A2 6/2006

OTHER PUBLICATIONS

Zhang,W., Wan,T. and Cao,X. NCBI GenBank Direct Submission May 15, 1999. CD40-like protein precursor [*Homo Sapiens*]. GenBank Acc. No. AAF75588.1.*

Ye Q, Fraser CC, Gao W, Wang L, Busfield SJ, Wang C, Qiu Y, Coyle AJ, Gutierrez-Ramos JC, Hancock WW. Modulation of LIGHT-HVEM costimulation prolongs cardiac allograft survival. J Exp Med. Mar. 18, 2002;195(6):795-800.*
Cheung TC, et. al. Ware CF. Evolutionarily divergent herpesviruses modulate T cell activation by targeting the herpesvirus entry mediator cosignaling pathway. Proc Natl Acad Sci U S A. Sep. 13, 2005;102(37):13218-23. Epub Aug. 30, 2005.*
Steinberg MW, Cheung TC, Ware CF. The signaling networks of the herpesvirus entry mediator (TNFRSF14) in immune regulation. Immunol Rev. Nov. 2011;244(1):169-87.*
Cheung TC, Oborne LM, Steinberg MW, Macauley MG, Fukuyama S, Sanjo H, D'Souza C, Norris PS, Pfeffer K, Murphy KM, Kronenberg M, Spear PG, Ware CF. T cell intrinsic heterodimeric complexes between HVEM and BTLA determine receptivity to the surrounding microenvironment. J Immunol. Dec. 1, 2009;183(11):7286-96. Epub Nov. 13, 2009.*
Sedý JR, Spear PG, Ware CF. Cross-regulation between herpesviruses and the TNF superfamily members. Nat Rev Immunol. Nov. 2008;8(11):861-73.*
Ware CF, Sedý JR. TNF Superfamily Networks: bidirectional and interference pathways of the herpesvirus entry mediator (TNFSF14). Curr Opin Immunol. Oct. 2011;23(5):627-31. Epub Sep. 13, 2011.*
Cheung KJ, et. al. Horsman DE. Acquired TNFRSF14 mutations in follicular lymphoma are associated with worse prognosis. Cancer Res. Nov. 15, 2010;70(22):9166-74. Epub Sep. 30, 2010.*
Montgomery RI, Warner MS, Lum BJ, Spear PG. Herpes simplex virus-1 entry into cells mediated by a novel member of the TNF/NGF receptor family. Cell. Nov. 1, 1996;87(3):427-36.*
Kojima R, Kajikawa M, Shiroishi M, Kuroki K, Maenaka K. Molecular basis for herpesvirus entry mediator recognition by the human immune inhibitory receptor CD160 and its relationship to the cosignaling molecules BTLA and LIGHT. J Mol Biol. Nov. 4, 2011;413(4):762-72. Epub Sep. 19, 2011.*
Baek H, Kim JH, Noh YT, Kwon H. The soluble amino-terminal region of HVEM mediates efficient herpes simplex virus type 1 infection of gD receptor-negative cells. Virol J. Jan. 13, 2012;9:15.*
Kaye J. CD160 and BTLA: LIGHTs out for CD4+ T cells. Nat Immunol. Feb. 2008;9(2):122-4.*
Cai G, Freeman GJ. The CD160, BTLA, LIGHT/HVEM pathway: a bidirectional switch regulating T-cell activation. Immunol Rev. May 2009;229(1):244-58.*
del Rio ML, Lucas CL, Buhler L, Rayat G, Rodriguez-Barbosa JI. HVEM/LIGHT/BTLA/CD160 cosignaling pathways as targets for immune regulation. J Leukoc Biol. Feb. 2010;87(2):223-35. Epub Dec. 9, 2009.*
Cai G, Anumanthan A, Brown JA, Greenfield EA, Zhu B, Freeman GJ. CD160 inhibits activation of human CD4+ T cells through interaction with herpesvirus sentry mediator. Nat Immunol. Feb. 2008;9(2):176-85. doi: 10.1038/ni1554. Epub Jan. 13, 2008. Erratum in: Nat Immunol. May 2008;9(5):567.*
Paulos CM, June CH. Putting the brakes on BTLA in T cell-mediated cancer immunotherapy. J Clin Invest. Jan. 2010;120(1):76-80. Epub Dec. 28, 2009.*

(Continued)

*Primary Examiner* — Rachel B Gill
(74) *Attorney, Agent, or Firm* — DLA Piper LLP (US)

(57) ABSTRACT

Ligand-specific HVEM variants, compositions comprising such variants, and methods of treating inflammatory diseases comprising administering such variants, are provided.

28 Claims, 16 Drawing Sheets

(56) References Cited

OTHER PUBLICATIONS

Ware CF, Sedý JR. TNF Superfamily Networks: bidirectional and interference pathways of the herpesvirus entry mediator (TNFSF14). Curr Opin Immunol. Oct. 2011;23(5):627-31.*
Barakonyi et al., "Expression profiles of peripheral CD160+ lymphocytes during the course of healthy human pregnancy", *Am. J. Reprod. Immunol.*, 66(2):137-142 (2011).
Cai et al., "CD160 inhibits activation of human CD4+ T cells through interaction with herpesvirus entry mediator", *Nat. Immunol.*, 9(2):176-185 (2008).
Kojima et al., "Molecular basis for herpesvirus entry mediator recognition by the human immune inhibitory receptor CD160 and its relationship to the cosignaling molecules BTLA and LIGHT", *J. Mol. Biol.*, 413(4):762-772 (2011).
Wang et al., "The regulation of T cell homeostasis and autoimmunity by T cell-derived LIGHT", *J. Clin. Invest.*, 108(12):1771-1780 (2001).
International Search Report from PCT/US2012/65200.
Cai, Guifang et al.: "*The CD160, BTLA, LIGHT/HVEM pathway: a bidirectionalswitch regulating T-cell activation*"; Immunological Reviews, vol. 229:1, May 1, 009, pp. 244-258.
Partial European Search Report dated Jun. 1, 2015, regarding EP 12 84 9803.
Del Rio, M. L. et al.: "*HVEM/LIGHT/BTLA/CD160 cosignaling pathways as targets for immune regulation*"; J. of Leukocyte Biology, vol. 87, No. 2, Dec. 9, 2009, pp. 223-235.
Sedy, J. R. et al.: "*CD160 Activation by Herpesvirus Entry Mediator Augments Inflammatory Cytokine Production and Cytolytic Function by NK Cells*"; J. of Immunology, vol. 191, No. 2, Jul. 15, 2013, pp. 828-836.
Extended European Search Report dated Oct. 7, 2015, regarding EP 12 849 803.7.

* cited by examiner

| HVEM mutant | BTLA | CD160 | LIGHT | Region |
|---|---|---|---|---|
| Wildtype | ++ | ++ | ++ | |
| G232S | ++ | ++ | ++ | Cyto |
| V215D | + | + | + | TM |
| R109W | ++ | -- | + | CRD2 |
| A102P | + | - | + | CRD2 |
| Ins91I | - | - | - | CRD2 |
| T82P | -- | -- | -- | CRD2 |
| G72P | -- | - | + | CRD1 |
| Y61C | -- | - | ++ | CRD1 |
| G60D | -- | -- | -- | CRD1 |
| P59S | ++ | - | ++ | CRD1 |

FIGURE 12

HVEM (TNFRSF14) AMINO ACID SEQUENCE

```
1    MEPPGDWGPP PWRSTPKTDV LRLVLYLTFL GAPCYAPALPSCKEDEYPVG
51   SECCPKCSPG YRVKEACGEL TGTVCEPCPP GTYIAHLNGLSKCLQCQMCD
101  PAMGLRASRN CSRTENAVCG CSPGHFCIVQ DGDHCAACRAYATSSPGQRV
151  QKGGTESQDT LCQNCPPGTF SPNGTLEECQ HQTKCSWLVTKAGAGTSSSH
201  WVWWFLSGSL VIVIVCSTVG LIICVKRRKP RGDVVKVIVS VQRKRQEAEG
251  EATVIEALQA PPDVTTVAVE ETIPSFTGRS PNH
```

Figure 16

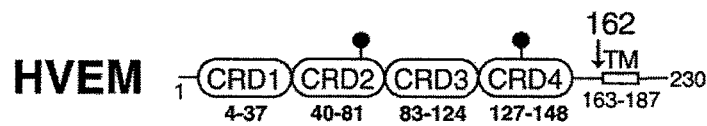

Figure 17

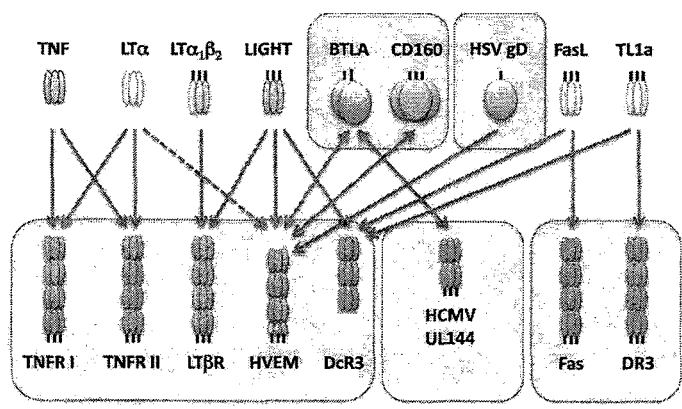

Figure 18

SEQUENCE LISTING

```
<160> NUMBER OF SEQ ID NOS: 82

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
agtcagatct gcgtgcagga tgctgttg                                          28

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
agtcctcgag ggcttacaaa gcttgaaggg                                        30

<210> SEQ ID NO 3
<211> LENGTH: 31
<212> TYPE: DNA
<213> ORGANISM: Artificial Sequence
<220> FEATURE:
```

<223> OTHER INFORMATION: Primer

<400> SEQUENCE: 3
agtcagatct gtgcaggaaa tgaagacatt g                31

<210> SEQ ID NO 4
<211> LENGTH: 36
<212> TYPE: DNA
<213> ORGANISM: Artificial Sequence
<220> FEATURE:
<223> OTHER INFORMATION: Primer

<400> SEQUENCE: 4
agtcctcgag tcagaaacag acttaactcc tcacac           36

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
agctagatct gcgtgcagga tgctgatg                    28

<210> SEQ ID NO 6
<211> LENGTH: 34
<212> TYPE: DNA
<213> ORGANISM: Artificial Sequence
<220> FEATURE:
<223> OTHER INFORMATION: Primer

<400> SEQUENCE: 6
agtcctcgag aaggcttaca aagcttgaag gacc             34

<210> SEQ ID NO 7
<211> LENGTH: 32
<212> TYPE: DNA
<213> ORGANISM: Artificial Sequence
<220> FEATURE:
<223> OTHER INFORMATION: Primer

<400> SEQUENCE: 7
aaacccgaag cagtgcaatt aggaaatcag tg               32

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
taattgcact gcttcgggtt tgcatatttc ag               32

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
ttaggaaatg cgtgttgtcc cccatgtaaa caag             34

```
<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
gggacaacac gcatttccta attgcacttc ttc                            33

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
cagtgttgtg ccccatgtaa acaaggatat cgtg                           34

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
tttacatggg gcacaacact gatttcctaa ttg                            33

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
tgtaaacaag catatcgtgt tacaggacaa tgtac                          35

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
aacacgatat gcttgtttac atgggggaca acactg                         36

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
cccccatgta acaaggagc tcgtgttaca ggacaatg                        38

<210> SEQ ID NO 16
<211> LENGTH: 38
<212> TYPE: DNA
<213> ORGANISM: Artificial Sequence
<220> FEATURE:
<223> OTHER INFORMATION: Primer
```

```
<400> SEQUENCE: 16
cattgtcctg taacacgagc tccttgttta catggggg                              38

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
caaggatatg ctgttacagg acaatgtacg caatatac                              38

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
tcctgtaaca gcatatcctt gtttacatgg ggg                                   33

<210> SEQ ID NO 19
<211> LENGTH: 33
<212> TYPE: DNA
<213> ORGANISM: Artificial Sequence
<220> FEATURE:
<223> OTHER INFORMATION: Primer

<400> SEQUENCE: 19
tatcgtgttg caggacaatg tacgcaatat acg                                   33

<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
acattgtcct gcaacacgat atccttgttt acatgg                                36

<210> SEQ ID NO 21
<211> LENGTH: 35
<212> TYPE: DNA
<213> ORGANISM: Artificial Sequence
<220> FEATURE:
<223> OTHER INFORMATION: Primer

<400> SEQUENCE: 21
cgtgttacag cacaatgtac gcaatatacg agtac                                 35

<210> SEQ ID NO 22
<211> LENGTH: 35
<212> TYPE: DNA
<213> ORGANISM: Artificial Sequence
<220> FEATURE:
<223> OTHER INFORMATION: Primer

<400> SEQUENCE: 22
cgtacattgt gctgtaacac gatatccttg tttac                                 35

<210> SEQ ID NO 23
<211> LENGTH: 45
```

```
<212> TYPE: DNA
<213> ORGANISM: Artificial Sequence
<220> FEATURE:
<223> OTHER INFORMATION: Primer

<400> SEQUENCE: 23
aaacaaggat atcgtgttac aaaacaatgt acgcaatata cgagt            45

<210> SEQ ID NO 24
<211> LENGTH: 45
<212> TYPE: DNA
<213> ORGANISM: Artificial Sequence
<220> FEATURE:
<223> OTHER INFORMATION: Primer

<400> SEQUENCE: 24
actcgtatat tgcgtacatt gttttgtaac acgatatcct tgttt            45

<210> SEQ ID NO 25
<211> LENGTH: 34
<212> TYPE: DNA
<213> ORGANISM: Artificial Sequence
<220> FEATURE:
<223> OTHER INFORMATION: Primer

<400> SEQUENCE: 25
caatgtacgg catatacgag tacaacatgt acag                         34

<210> SEQ ID NO 26
<211> LENGTH: 38
<212> TYPE: DNA
<213> ORGANISM: Artificial Sequence
<220> FEATURE:
<223> OTHER INFORMATION: Primer

<400> SEQUENCE: 26
actcgtatat gccgtacatt gtcctgtaac acgatatc                     38

<210> SEQ ID NO 27
<211> LENGTH: 35
<212> TYPE: DNA
<213> ORGANISM: Artificial Sequence
<220> FEATURE:
<223> OTHER INFORMATION: Primer

<400> SEQUENCE: 27
acgcaatatg cgagtacaac atgtacactt tgccc                        35

<210> SEQ ID NO 28
<211> LENGTH: 36
<212> TYPE: DNA
<213> ORGANISM: Artificial Sequence
<220> FEATURE:
<223> OTHER INFORMATION: Primer

<400> SEQUENCE: 28
tgttgtactc gcatattgcg tacattgttc tgtaac                       36

<210> SEQ ID NO 29
<211> LENGTH: 34
<212> TYPE: DNA
<213> ORGANISM: Artificial Sequence
<220> FEATURE:
<223> OTHER INFORMATION: Primer

<400> SEQUENCE: 29
```

```
gtatcagggg cttacaattg taccaattgc actg                          34

<210> SEQ ID NO 30
<211> LENGTH: 35
<212> TYPE: DNA
<213> ORGANISM: Artificial Sequence
<220> FEATURE:
<223> OTHER INFORMATION: Primer

<400> SEQUENCE: 30
acaattgtaa gcccctgata catacgtacc gttag                         35

<210> SEQ ID NO 31
<211> LENGTH: 35
<212> TYPE: DNA
<213> ORGANISM: Artificial Sequence
<220> FEATURE:
<223> OTHER INFORMATION: Primer

<400> SEQUENCE: 31
ttttccgttg caggcgtcca acatcacaag caacg                         35

<210> SEQ ID NO 32
<211> LENGTH: 34
<212> TYPE: DNA
<213> ORGANISM: Artificial Sequence
<220> FEATURE:
<223> OTHER INFORMATION: Primer

<400> SEQUENCE: 32
ttggacgcct gcaacggaaa atgacgtata attc                          34

<210> SEQ ID NO 33
<211> LENGTH: 43
<212> TYPE: DNA
<213> ORGANISM: Artificial Sequence
<220> FEATURE:
<223> OTHER INFORMATION: Primer

<400> SEQUENCE: 33
catgtgatgt agcgctttat ataaagagac aatctgaaca ctc                43

<210> SEQ ID NO 34
<211> LENGTH: 39
<212> TYPE: DNA
<213> ORGANISM: Artificial Sequence
<220> FEATURE:
<223> OTHER INFORMATION: Primer

<400> SEQUENCE: 34
ctttatataa agcgctacat cacatgattc tttcccatg                     39

<210> SEQ ID NO 35
<211> LENGTH: 43
<212> TYPE: DNA
<213> ORGANISM: Artificial Sequence
<220> FEATURE:
<223> OTHER INFORMATION: Primer

<400> SEQUENCE: 35
atgtgatgta cagcattata taaagagaca atctgaacac tcc                43

<210> SEQ ID NO 36
<211> LENGTH: 41
<212> TYPE: DNA
<213> ORGANISM: Artificial Sequence
```

```
<220> FEATURE:
<223> OTHER INFORMATION: Primer

<400> SEQUENCE: 36
ttgtctcttt atataatgct gtacatcaca tgattctttc c                41

<210> SEQ ID NO 37
<211> LENGTH: 38
<212> TYPE: DNA
<213> ORGANISM: Artificial Sequence
<220> FEATURE:
<223> OTHER INFORMATION: Primer

<400> SEQUENCE: 37
ctttatataa aggaccaatc tgaacactcc atcttagc                    38

<210> SEQ ID NO 38
<211> LENGTH: 45
<212> TYPE: DNA
<213> ORGANISM: Artificial Sequence
<220> FEATURE:
<223> OTHER INFORMATION: Primer

<400> SEQUENCE: 38
gtgttcagat tggtccttta tataaagctg tacatcacat gattc            45

<210> SEQ ID NO 39
<211> LENGTH: 37
<212> TYPE: DNA
<213> ORGANISM: Artificial Sequence
<220> FEATURE:
<223> OTHER INFORMATION: Primer

<400> SEQUENCE: 39
agagacaatc tgcacactcc atcttagcag gagatcc                     37

<210> SEQ ID NO 40
<211> LENGTH: 41
<212> TYPE: DNA
<213> ORGANISM: Artificial Sequence
<220> FEATURE:
<223> OTHER INFORMATION: Primer

<400> SEQUENCE: 40
aagatggagt gtggagattg tctctttata taaagctgta c                41

<210> SEQ ID NO 41
<211> LENGTH: 37
<212> TYPE: DNA
<213> ORGANISM: Artificial Sequence
<220> FEATURE:
<223> OTHER INFORMATION: Primer

<400> SEQUENCE: 41
ctttgaacta gcatgccctg tgaaatactg tgctaac                     37

<210> SEQ ID NO 42
<211> LENGTH: 38
<212> TYPE: DNA
<213> ORGANISM: Artificial Sequence
<220> FEATURE:
<223> OTHER INFORMATION: Primer

<400> SEQUENCE: 42
tcacagggca tgctagttca aagggatctc ctgctaag                    38
```

<210> SEQ ID NO 43
<211> LENGTH: 37
<212> TYPE: DNA
<213> ORGANISM: Artificial Sequence
<220> FEATURE:
<223> OTHER INFORMATION: Primer

<400> SEQUENCE: 43
gaactagaat gcgctgtgaa atactgtgct aacaggc         37

<210> SEQ ID NO 44
<211> LENGTH: 35
<212> TYPE: DNA
<213> ORGANISM: Artificial Sequence
<220> FEATURE:
<223> OTHER INFORMATION: Primer

<400> SEQUENCE: 44
gtatttcaca gcgcattcta gttcaaaggg atctc         35

<210> SEQ ID NO 45
<211> LENGTH: 40
<212> TYPE: DNA
<213> ORGANISM: Artificial Sequence
<220> FEATURE:
<223> OTHER INFORMATION: Primer

<400> SEQUENCE: 45
acaagttggg cggaagagaa gaacatttca tttttcattc         40

<210> SEQ ID NO 46
<211> LENGTH: 42
<212> TYPE: DNA
<213> ORGANISM: Artificial Sequence
<220> FEATURE:
<223> OTHER INFORMATION: Primer

<400> SEQUENCE: 46
cttctcttcc gcccaacttg tttgtctatc ttcaagtttt ac         42

<210> SEQ ID NO 47
<211> LENGTH: 36
<212> TYPE: DNA
<213> ORGANISM: Artificial Sequence
<220> FEATURE:
<223> OTHER INFORMATION: Primer

<400> SEQUENCE: 47
tgttctgcaa attttcagtc taatctcatt gaaagc         36

<210> SEQ ID NO 48
<211> LENGTH: 37
<212> TYPE: DNA
<213> ORGANISM: Artificial Sequence
<220> FEATURE:
<223> OTHER INFORMATION: Primer

<400> SEQUENCE: 48
gattagactg aaaatttgca gaacagcggt atgaccc         37

<210> SEQ ID NO 49
<211> LENGTH: 38
<212> TYPE: DNA
<213> ORGANISM: Artificial Sequence
<220> FEATURE:
<223> OTHER INFORMATION: Primer

<400> SEQUENCE: 49
gctgttctgc attttttcag tctaatctca ttgaaagc                                38

<210> SEQ ID NO 50
<211> LENGTH: 32
<212> TYPE: DNA
<213> ORGANISM: Artificial Sequence
<220> FEATURE:
<223> OTHER INFORMATION: Primer

<400> SEQUENCE: 50
tagactgaaa aaatgcagaa cagcggtatg ac                                      32

<210> SEQ ID NO 51
<211> LENGTH: 38
<212> TYPE: DNA
<213> ORGANISM: Artificial Sequence
<220> FEATURE:
<223> OTHER INFORMATION: Primer

<400> SEQUENCE: 51
gttctgcaaa tgctcagtct aatctcattg aaagccac                                38

<210> SEQ ID NO 52
<211> LENGTH: 35
<212> TYPE: DNA
<213> ORGANISM: Artificial Sequence
<220> FEATURE:
<223> OTHER INFORMATION: Primer

<400> SEQUENCE: 52
gagattagac tgagcatttg cagaacagcg gtatg                                   35

<210> SEQ ID NO 53
<211> LENGTH: 37
<212> TYPE: DNA
<213> ORGANISM: Artificial Sequence
<220> FEATURE:
<223> OTHER INFORMATION: Primer

<400> SEQUENCE: 53
caaattttca gcataatctc attgaaagcc actcaac                                 37

<210> SEQ ID NO 54
<211> LENGTH: 34
<212> TYPE: DNA
<213> ORGANISM: Artificial Sequence
<220> FEATURE:
<223> OTHER INFORMATION: Primer

<400> SEQUENCE: 54
caatgagatt atgctgaaaa tttgcagaac agcg                                    34

<210> SEQ ID NO 55
<211> LENGTH: 38
<212> TYPE: DNA
<213> ORGANISM: Artificial Sequence
<220> FEATURE:
<223> OTHER INFORMATION: Primer

<400> SEQUENCE: 55
cattgaaagc gactcaacaa ctctttatgt gacagatg                                38

<210> SEQ ID NO 56

```
<211> LENGTH: 40
<212> TYPE: DNA
<213> ORGANISM: Artificial Sequence
<220> FEATURE:
<223> OTHER INFORMATION: Primer

<400> SEQUENCE: 56
gttgttgagt cgctttcaat gagattagac tgaaaatttg                             40

<210> SEQ ID NO 57
<211> LENGTH: 42
<212> TYPE: DNA
<213> ORGANISM: Artificial Sequence
<220> FEATURE:
<223> OTHER INFORMATION: Primer

<400> SEQUENCE: 57
tgaaagccac catacaactc tttatgtgac agatgtaaaa ag                          42

<210> SEQ ID NO 58
<211> LENGTH: 36
<212> TYPE: DNA
<213> ORGANISM: Artificial Sequence
<220> FEATURE:
<223> OTHER INFORMATION: Primer

<400> SEQUENCE: 58
aagagttgta tggtggcttt caatgagatt agactg                                 36

<210> SEQ ID NO 59
<211> LENGTH: 18
<212> TYPE: DNA
<213> ORGANISM: Artificial Sequence
<220> FEATURE:
<223> OTHER INFORMATION: Primer

<400> SEQUENCE: 59
actaccgccc agcagtgt                                                     18

<210> SEQ ID NO 60
<211> LENGTH: 19
<212> TYPE: DNA
<213> ORGANISM: Artificial Sequence
<220> FEATURE:
<223> OTHER INFORMATION: Primer

<400> SEQUENCE: 60
gtgtcatggg gagaaccaa                                                    19

<210> SEQ ID NO 61
<211> LENGTH: 18
<212> TYPE: DNA
<213> ORGANISM: Artificial Sequence
<220> FEATURE:
<223> OTHER INFORMATION: Primer

<400> SEQUENCE: 61
ggcggtgcct atcactgt                                                     18

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
```

```
ttctgaaacc ccagtccttg                                              20

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
tctcttgctg ttgctgatgg                                              20

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
ctcgtgagac cttcgctctt                                              20

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
cagcctcttc tccttcctga t                                            21

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
gccagagggc tgattagaga                                              20

<210> SEQ ID NO 67
<211> LENGTH: 21
<212> TYPE: DNA
<213> ORGANISM: Artificial Sequence
<220> FEATURE:
<223> OTHER INFORMATION: Primer

<400> SEQUENCE: 67
agcagctccc cactgggtat g                                            21

<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68
gattaggcca actgtggagc a                                            21

<210> SEQ ID NO 69
<211> LENGTH: 26
<212> TYPE: DNA
```

```
<213> ORGANISM: Artificial Sequence
<220> FEATURE:
<223> OTHER INFORMATION: Primer

<400> SEQUENCE: 69
gcctctactc atcactacct gttttc                                          26

<210> SEQ ID NO 70
<211> LENGTH: 23
<212> TYPE: DNA
<213> ORGANISM: Artificial Sequence
<220> FEATURE:
<223> OTHER INFORMATION: Primer

<400> SEQUENCE: 70
tcagagagtt cattttgctt tcc                                             23

<210> SEQ ID NO 71
<211> LENGTH: 22
<212> TYPE: DNA
<213> ORGANISM: Artificial Sequence
<220> FEATURE:
<223> OTHER INFORMATION: Primer

<400> SEQUENCE: 71
cctcactaca tccgtgaact cc                                              22

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
ctgctggtat ccttggcttc                                                 20

<210> SEQ ID NO 73
<211> LENGTH: 19
<212> TYPE: DNA
<213> ORGANISM: Artificial Sequence
<220> FEATURE:
<223> OTHER INFORMATION: Primer

<400> SEQUENCE: 73
cccctggttg ttgtagcag                                                  19

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
gtaggaggtg cgagttcagg                                                 20

<210> SEQ ID NO 75
<211> LENGTH: 19
<212> TYPE: DNA
<213> ORGANISM: Artificial Sequence
<220> FEATURE:
<223> OTHER INFORMATION: Primer

<400> SEQUENCE: 75
cttcgactgc gtgctcaag                                                  19
```

<210> SEQ ID NO 76
<211> LENGTH: 18
<212> TYPE: DNA
<213> ORGANISM: Artificial Sequence
<220> FEATURE:
<223> OTHER INFORMATION: Primer

<400> SEQUENCE: 76
gtaggtggcg aggggaag                                                 18

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
ggatctggcc cttgaacctt                                               20

<210> SEQ ID NO 78
<211> LENGTH: 18
<212> TYPE: DNA
<213> ORGANISM: Artificial Sequence
<220> FEATURE:
<223> OTHER INFORMATION: Primer

<400> SEQUENCE: 78
gaaactggcg gaaaccca                                                 18

<210> SEQ ID NO 79
<211> LENGTH: 283
<212> TYPE: PRT
<213> ORGANISM: Homo sapiens

<400> SEQUENCE: 79

Met Glu Pro Pro Gly Asp Trp Gly Pro Pro Trp Arg Ser Thr Pro
1               5                   10                  15

Lys Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala

```
                        180                 185                 190
Gly Ala Gly Thr Ser Ser His Trp Val Trp Trp Phe Leu Ser Gly
            195                 200                 205

Ser Leu Val Ile Val Ile Val Cys Ser Thr Val Gly Leu Ile Ile Cys
            210                 215                 220

Val Lys Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
            275                 280

<210> SEQ ID NO 80
<211> LENGTH: 78
<212> TYPE: PRT
<213> ORGANISM: Homo sapiens

<400> SEQUENCE: 80

Cys Lys Glu Asp Glu Tyr Pro Val Gly Ser Cys Cys Pro Lys Cys
1               5                   10                  15

Ser Pro Gly Tyr Arg Val Lys Glu Ala Cys Gly Glu Leu Thr Gly Thr
                20                  25                  30

Val Cys Glu Pro Cys Pro Pro Gly Thr Tyr Ile Ala His Leu Asn Gly
            35                  40                  45

Leu Ser Lys Cys Leu Gln Cys Gln Met Cys Asp Pro Ala Met Gly Leu
50                  55                  60

Arg Ala Ser Arg Asn Cys Ser Arg Thr Glu Asn Ala Val Cys
65                  70                  75

<210> SEQ ID NO 81
<211> LENGTH: 73
<212> TYPE: PRT
<213> ORGANISM: Human herpesvirus 5

<400> SEQUENCE: 81

Cys Lys Pro Glu Glu Val Gln Leu Gly Asn Gln Cys Cys Pro Pro Cys
1               5                   10                  15

Lys Gln Gly Tyr Arg Val Thr Gly Gln Cys Thr Gln Tyr Thr Ser Thr
                20                  25                  30

Thr Cys Thr Leu Cys Pro Asn Gly Thr Tyr Val Ser Gly Leu Tyr Asn
            35                  40                  45

Cys Thr Asn Cys Thr Glu Cys Asn Asp Thr Glu Val Thr Ile Arg Asn
50                  55                  60

Cys Thr Ser Thr Asn Asn Thr Val Cys
65                  70

<210> SEQ ID NO 82
<211> LENGTH: 78
<212> TYPE: PRT
<213> ORGANISM: Artificial Sequence
<220> FEATURE:
<223> OTHER INFORMATION: Synthetic construct: Consensus sequence
<220> FEATURE:
<221> NAME/KEY: MISC_FEATURE
<222> LOCATION: (3)..(3)
<223> OTHER INFORMATION: Xaa is E or P
<220> FEATURE:
<221> NAME/KEY: MISC_FEATURE
```

```
<222> LOCATION: (4)..(4)
<223> OTHER INFORMATION: Xaa is D or E
<220> FEATURE:
<221> NAME/KEY: MISC_FEATURE
<222> LOCATION: (6)..(6)
<223> OTHER INFORMATION: Xaa is Y or V
<220> FEATURE:
<221> NAME/KEY: MISC_FEATURE
<222> LOCATION: (7)..(7)
<223> OTHER INFORMATION: Xaa is P or Q
<220> FEATURE:
<221> NAME/KEY: MISC_FEATURE
<222> LOCATION: (8)..(8)
<223> OTHER INFORMATION: Xaa is V or L
<220> FEATURE:
<221> NAME/KEY: MISC_FEATURE
<222> LOCATION: (10)..(10)
<223> OTHER INFORMATION: Xaa is S or N
<220> FEATURE:
<221> NAME/KEY: MISC_FEATURE
<222> LOCATION: (11)..(11)
<223> OTHER INFORMATION: Xaa is E or Q
<220> FEATURE:
<221> NAME/KEY: MISC_FEATURE
<222> LOCATION: (15)..(15)
<223> OTHER INFORMATION: Xaa is K or P
<220> FEATURE:
<221> NAME/KEY: MISC_FEATURE
<222> LOCATION: (17)..(17)
<223> OTHER INFORMATION: Xaa is S or K
<220> FEATURE:
<221> NAME/KEY: MISC_FEATURE
<222> LOCATION: (18)..(18)
<223> OTHER INFORMATION: Xaa is P or Q
<220> FEATURE:
<221> NAME/KEY: MISC_FEATURE
<222> LOCATION: (23)..(23)
<223> OTHER INFORMATION: Xaa is K or T
<220> FEATURE:
<221> NAME/KEY: MISC_FEATURE
<222> LOCATION: (24)..(24)
<223> OTHER INFORMATION: Xaa is E or G
<220> FEATURE:
<221> NAME/KEY: MISC_FEATURE
<222> LOCATION: (25)..(25)
<223> OTHER INFORMATION: Xaa is A or Q
<220> FEATURE:
<221> NAME/KEY: MISC_FEATURE
<222> LOCATION: (27)..(27)
<223> OTHER INFORMATION: Xaa is G or T
<220> FEATURE:
<221> NAME/KEY: MISC_FEATURE
<222> LOCATION: (28)..(28)
<223> OTHER INFORMATION: Xaa is E or Q
<220> FEATURE:
<221> NAME/KEY: MISC_FEATURE
<222> LOCATION: (29)..(29)
<223> OTHER INFORMATION: Xaa is L or Y
<220> FEATURE:
<221> NAME/KEY: MISC_FEATURE
<222> LOCATION: (31)..(31)
<223> OTHER INFORMATION: Xaa is G or S
<220> FEATURE:
<221> NAME/KEY: MISC_FEATURE
<222> LOCATION: (33)..(33)
<223> OTHER INFORMATION: Xaa is V or T
<220> FEATURE:
<221> NAME/KEY: MISC_FEATURE
<222> LOCATION: (35)..(35)
<223> OTHER INFORMATION: Xaa is E or T
<220> FEATURE:
<221> NAME/KEY: MISC_FEATURE
<222> LOCATION: (36)..(36)
<223> OTHER INFORMATION: Xaa is P or L
<220> FEATURE:
<221> NAME/KEY: MISC_FEATURE
<222> LOCATION: (39)..(39)
<223> OTHER INFORMATION: Xaa is P or N
<220> FEATURE:
```

```
<221> NAME/KEY: MISC_FEATURE
<222> LOCATION: (43)..(43)
<223> OTHER INFORMATION: Xaa is I or V
<220> FEATURE:
<221> NAME/KEY: MISC_FEATURE
<222> LOCATION: (44)..(44)
<223> OTHER INFORMATION: Xaa is A or S
<220> FEATURE:
<221> NAME/KEY: MISC_FEATURE
<222> LOCATION: (50)..(50)
<223> OTHER INFORMATION: Xaa is S or Y
<220> FEATURE:
<221> NAME/KEY: MISC_FEATURE
<222> LOCATION: (51)..(51)
<223> OTHER INFORMATION: Xaa is K or N
<220> FEATURE:
<221> NAME/KEY: MISC_FEATURE
<222> LOCATION: (53)..(53)
<223> OTHER INFORMATION: Xaa is L or T
<220> FEATURE:
<221> NAME/KEY: MISC_FEATURE
<222> LOCATION: (54)..(54)
<223> OTHER INFORMATION: Xaa is Q or N
<220> FEATURE:
<221> NAME/KEY: MISC_FEATURE
<222> LOCATION: (56)..(56)
<223> OTHER INFORMATION: Xaa is Q or T
<220> FEATURE:
<221> NAME/KEY: MISC_FEATURE
<222> LOCATION: (57)..(57)
<223> OTHER INFORMATION: Xaa is M or E
<220> FEATURE:
<221> NAME/KEY: MISC_FEATURE
<222> LOCATION: (59)..(59)
<223> OTHER INFORMATION: Xaa is D or N
<220> FEATURE:
<221> NAME/KEY: MISC_FEATURE
<222> LOCATION: (60)..(60)
<223> OTHER INFORMATION: Xaa is P or D
<220> FEATURE:
<221> NAME/KEY: MISC_FEATURE
<222> LOCATION: (61)..(61)
<223> OTHER INFORMATION: Xaa is A or T
<220> FEATURE:
<221> NAME/KEY: MISC_FEATURE
<222> LOCATION: (62)..(62)
<223> OTHER INFORMATION: Xaa is M or E
<220> FEATURE:
<221> NAME/KEY: MISC_FEATURE
<222> LOCATION: (65)..(65)
<223> OTHER INFORMATION: Xaa is R or V
<220> FEATURE:
<221> NAME/KEY: MISC_FEATURE
<222> LOCATION: (66)..(66)
<223> OTHER INFORMATION: Xaa is A or T
<220> FEATURE:
<221> NAME/KEY: MISC_FEATURE
<222> LOCATION: (67)..(67)
<223> OTHER INFORMATION: Xaa is S or I
<220> FEATURE:
<221> NAME/KEY: MISC_FEATURE
<222> LOCATION: (71)..(71)
<223> OTHER INFORMATION: Xaa is S or T
<220> FEATURE:
<221> NAME/KEY: MISC_FEATURE
<222> LOCATION: (72)..(72)
<223> OTHER INFORMATION: Xaa is R or S
<220> FEATURE:
<221> NAME/KEY: MISC_FEATURE
<222> LOCATION: (74)..(74)
<223> OTHER INFORMATION: Xaa is E or N
<220> FEATURE:
<221> NAME/KEY: MISC_FEATURE
<222> LOCATION: (76)..(76)
<223> OTHER INFORMATION: Xaa is A or T

<400> SEQUENCE: 82

Cys Lys Xaa Xaa Glu Xaa Xaa Xaa Gly Xaa Xaa Cys Cys Pro Xaa Cys
```

```
1               5                    10                   15
Xaa Xaa Gly Tyr Arg Val Xaa Xaa Xaa Cys Xaa Xaa Xaa Thr Xaa Thr
                20                   25                  30

Xaa Cys Xaa Xaa Cys Pro Xaa Gly Thr Tyr Xaa Xaa His Leu Asn Gly
        35                  40                  45

Leu Xaa Xaa Cys Xaa Xaa Cys Xaa Xaa Cys Xaa Xaa Xaa Gly Leu
    50                  55                  60

Xaa Xaa Xaa Arg Asn Cys Xaa Xaa Thr Xaa Asn Xaa Val Cys
65                  70                  75
```

COMPOSITIONS AND METHODS FOR TREATING AUTOIMMUNE AND INFLAMMATORY DISORDERS

CROSS-REFERENCE TO RELATED APPLICATIONS

This application claims benefit of priority under 35 U.S.C. § 119(e) of U.S. Ser. No. 61/597,634, filed Feb. 10, 2012; and U.S. Ser. No. 61/560,081, filed Nov. 15, 2011, the entire contents of which are incorporated herein by reference in their entireties.

STATEMENT OF GOVERNMENT RIGHTS

This invention was made in part with Government support under National Institutes of Health grants AI067890 and AI033068. The Government has certain rights to the invention.

BACKGROUND

Field of Invention

The present invention relates generally to biotherapeutics directed at the inhibitory co-signaling receptor, BTLA and more specifically to therapeutic indications including autoimmune and inflammatory disorders.

Background Information

In healthy individuals the natural inflammatory response to infections and cancer is tightly regulated by a number of positive and negative control mechanisms on multiple cell lineages. This regulation can at times be co-opted by specific infectious agents or when specific pathways are compromised by somatic mutations leading to diseases of inflammatory pathogenesis. Activation of TNFRSF14 (Herpesvirus entry mediator, —HVEM) within various tissues by its ligands LIGHT (TNFSF14), BTLA (B and T Lymphocyte Attenuator), and CD160 leads to a broad range of inflammation countered by the activation of lymphocyte expressed BTLA by HVEM. CD160 shows more restricted cellular expression on natural killer cells and cytotoxic T cells and was reported to also inhibit lymphocytes responses. However, it has been determined that CD160 activates positive signals in lymphocytes in response to HVEM ligation.

Tumor necrosis factor inhibitors including the decoy receptor etanercept and antibodies (eg., adalimumab) have shown significant responses in patients with autoimmune diseases. TNF inhibitors are effective in 30-40% of patients with rheumatoid arthritis and other autoimmune diseases. However, a majority of patients show a partial or no response to this class of drugs. The basis of this failure to respond to TNF inhibitors remains unexplained. The mechanism of action of the TNF inhibitors is direct blockade of TNF binding to its receptors, halting a proinflammatory pathway. The main effect of blocking TNF is to quell innate inflammatory cells, but T cells may not be impacted, and TNF blockade alone may not reestablish homeostasis. The present invention targets a specific inhibitory pathway to attenuate inflammatory pathways and pathologic immune responses.

Substantial evidence indicates that HVEM is critically important when expressed in mucosal epithelium to suppress inflammation mediated by autoreactive T cells and macrophages. In a mouse model of Crohn's Disease, the loss of TNFSF14 in epithelium dramatically accelerated the onset of intestinal inflammation; BTLA expression in T cells and innate effector cells was required to suppress inflammation. These results established the physiological relevance of the HVEM-BTLA signaling pathway between different organs. In a chronic lung inflammation model of asthma, the LIGHT-HVEM system revealed itself as an essential pathway for memory T cells that drive pathology to persist in the lung. Moreover, LIGHT-LTβR pathway drives pathologic lung remodeling. These attributes place the HVEM system in a unique position to regulate immune responses. While the use of biologic intervention to target these pathways has led to some success in controlling HVEM mediated inflammation, it has previously been difficult to discriminate tissue and cell-specific effects due to the complexity of ligand interactions and the variability in response from specific targets.

Inflammatory responses to infections and cancer are regulated by a number of positive and negative control mechanisms on multiple cell lineages. Natural killer (NK) cells are an essential component of the innate immune system that protect against a wide range of pathogens, particularly against herpesviruses. Mature NK cells express a diverse array of receptors that activate cytolysis and cytokine release. NK cell activation is balanced by an equally varied number of inhibitory receptors that prevent uncontrolled cytolysis and inflammation through the recognition of self major histocompatibility complex (MHC) molecules in healthy, uninfected cells.

Many herpesviruses have manipulated this balance in order to prevent clearance of infected cells, allowing for viral replication and the establishment of latency. In order to become fully functional effector cells receptive to activating ligands, NK cells develop and are primed in response to the cytokine IL-15, and to a lesser extent IL-2 in vivo, both of which activate common γ chain signaling. IL-2 and IL-15 also induce the expression of antiviral interferon-γ and surface lymphotoxin (LT)-αβ.

Recent studies have shown that somatic mutations in TNFRSF14 either through deletion or nonsysnonymous mutation are among the most common gene alterations in follicular and diffuse large B cell lymphoma. Follicular lymphoma harboring acquired TNFRSF14 mutations are associated with worse prognosis, highlighting the anti-inflammatory effect of HVEM in the tumor microenvironment. While the mechanism for the tumor suppressive role of HVEM is unclear, the absence of NK cell and cytotoxic T cell costimulation through CD160 may lead to aborted anti-tumor responses. Alternatively, the absence of HVEM would prevent inhibition of T cells expressing BTLA, thus promoting the release of B cell growth factors. Finally, the absence of HVEM may act in a cell intrinsic manner in tumor cells to prevent the initiation of death signals. Additionally, lymphoma bearing HVEM deletions would express BTLA alone and not in a complex with HVEM, and thus would be exposed to ligands from other cells, antibodies or biologics which could drive inhibitory signals to the tumor cell.

The HVEM (TNFRSF14) (EMBL-CDS: AAQ89238.1: *Homo sapiens* (human) HVEM is a member of the tumor necrosis factor receptor superfamily expressed on lymphocytes, regulates immune responses by activating both proinflammatory and inhibitory signaling pathways (alternatively, one of skill in the art can use other known HVEM sequences, such as (Genentech) or the NCBI sequence, which may differ by 1 base (e.g., a Lys to Arg change at position 16 in the signal sequence (not in the mature protein)). HVEM binds the TNF-related ligands LIGHT (TNFSF14) and LT-α, and the immunoglobulin domain containing receptors B and T lymphocyte attenuator (BTLA). BTLA activation results in phosphorylation of its cytoplasmic tyrosines and recruitment of the tyrosine phosphatases Src homology domain 2 containing phosphatase-1 (SHP1) and 2, resulting in diminished antigen receptor signaling in T cells and B cells. In contrast, CD160 both activates NK cells and acts as an inhibitory receptor on a subset of $CD4^+$ T cells. In T cells, LIGHT-HVEM signaling enhances antigen induced T cell proliferation and cytokine production.

Human Cytomegalovirus (CMV), a β-herpesvirus, contains a number of genes that modulate host immune responses and specifically NK cell activation. Many of these genes are encoded within the unique long subregion $(U_L)$/b' of the CMV genome that is not essential for replication in vitro The UL144 open reading frame contained within the $(U_L)$/b' locus was first identified as an expressed transcript encoding a type 1 transmembrane protein and as an ortholog to HVEM. UL144 does not bind LIGHT or LT-α, presumably because it lacks the third and fourth cysteine-rich domains (CRD) contained in HVEM, although it does bind and activate BTLA via CRD1 to restrain T cell proliferation.

Because HVEM activates both proinflammatory and inhibitory signaling pathways, HVEM has an important role in regulating inflammation. Additional evidence supports the importance of HVEM's role. For example, HVEM plays a role in suppression of inflammation mediated by autoreactive T cells and macrophages in mucosal epithelium. In a mouse model of Crohn's disease, the loss of HVEM in epithelium dramatically accelerated the onset of intestinal inflammation; BTLA expression in T cells and innate effector cells was required to suppress inflammation. In a chronic lung inflammation model of asthma, the LIGHT-HVEM system is an essential pathway for memory T cells that drive pathology in the lung. Moreover, the LIGHT-LTβR pathway drives pathologic lung remodeling and the HVEM-BTLA system can counteregulate the LTβR pathway.

A ligand-specific HVEM protein, including a ligand-specific HVEM protein that binds to BTLA but not to LIGHT or CD160, would be useful for treating inflammatory diseases and may also be useful for suppressing growth of BTLA expressing tumor cells. An HVEM specific for CD160 may provide activating signals that induce innate lymphocytes, such as NK cells, or T cells to arrest the growth or kill tumor cells.

SUMMARY

The present disclosure includes an understanding of a cytokine pathway that controls both proinflammatory and inhibitory signaling in T and B cells, antigen-presenting dendritic cells, and innate lymphoid cells, and methods of use of the same. TNFRSF14 or herpesvirus entry mediator (HVEM) serves as a molecular switch between proinflammatory and inhibitory signaling because it binds two distinct classes of ligands: LIGHT, a TNF related ligand is highly inflammatory in its membrane bound form and Lymphotoxin-α. TNFRSF14 also engages BTLA (B and T lymphocyte attenuator) an Ig superfamily member that activates inhibitory signaling, and CD160. TNFRSF14 is part of the wider TNF/lymphotoxin network (FIG. 18). This complex network of signaling pathways is defined by shared ligands and receptors. Although at first glance these pathways appear redundant, surprisingly evidence indicates that each pathway holds intrinsic regulatory function with unique biologic impact. The present disclosure provides a series of novel mutations within HVEM that show specificity for each ligand and are able to distinguish pro-inflammatory versus inhibitory responses and methods of using the same. The present invention shows that HVEM-Fc is stimulatory to activation of NK cells and that HVEM variants which bind and engage BTLA but do not bind CD160 are inhibitory to activation of NK cells.

The present disclosure is based on the discovery that the Cytomegalovirus protein UL144, which is a structural and functional mimic of HVEM, specifically selects for BTLA binding and inhibits natural killer cell activation through BTLA without binding CD160. The present invention includes methods employing the discovery that HVEM variants and UL144-Fc can be used to inhibit natural killer cell activation in a broad spectrum of inflammatory and auto-immune diseases, as well as cancer.

In one aspect, the invention provides an isolated HVEM polypeptide variant, wherein the variant binds to BTLA and does not bind to CD160. In certain embodiments, the variant does not bind to CD160, LIGHT or LTα.

In one embodiment, the HVEM polypeptide variant includes a wild-type HVEM protein (SEQ ID NO: 79) having one or more amino acid substitutions at residue position 59, 60, 61, 72, 82, 109, 232 or any combination thereof.

In certain embodiments, the HVEM polypeptide variant includes a wild-type HVEM protein with an amino acid substitution at position 109. In another embodiment, the variant includes a wild-type HVEM protein with an amino acid substitution at position 59. In another embodiments the variant includes HVEM R109W. In another embodiment the variant includes HVEM P59S. In various embodiments, the variant is a truncation of a wild-type HVEM protein which includes the extracellular domain of HVEM or a portion thereof, having one or more cysteine rich domains (CRDs). In another embodiment, the variant further includes a suitable dimerizing domain, such as IgG1 Fc.

In one embodiment, binding of the HVEM polypeptide variant to an HVEM ligand, such as BTLA, inhibits IL-2 signaling. In another embodiment, binding of the variant to an HVEM ligand, such as BTLA, reduces expression of LT-β and interferon-γ.

In another aspect, a pharmaceutical composition comprising an isolated HVEM polypeptide variant, wherein the variant binds to BTLA and does not bind to CD160, and a pharmaceutically acceptable carrier, is provided.

In another aspect, an isolated nucleic acid molecule encoding a HVEM polypeptide variant is provided.

In another aspect, an expression cassette including a nucleic acid molecule encoding a HVEM polypeptide variant is provided.

In another aspect, a host cell transformed or transfected with a nucleic acid molecule encoding a HVEM polypeptide variant is provided.

The disclosure also provides a method for treating an inflammatory or auto-immune disease in a subject. The method includes administering to a subject a pharmaceutical composition including an isolated HVEM polypeptide variant, wherein the variant binds to at least one ligand for HVEM, such as BTLA, and does not bind to at least one other ligand for HVEM, such as CD160, and a pharmaceutically acceptable carrier.

In another aspect, the disclosure provides a method of inhibiting a proinflammatory response in a subject comprising administering to the subject an agent which inhibits binding of herpesvirus entry mediator (HVEM) to CD160 or agonizes BTLA binding to HVEM. In various embodiments, the agent inhibits activation of natural killer (NK) cells and is a negative regulator of IL-2 signaling. In various embodiment, the agent is a polypeptide, antibody, or fragments thereof, UL144 or HVEM polypeptide variant as described herein. In certain embodiments, the agent specifically inhibits binding of HVEM to CD160 without inhibiting binding of HVEM to BTLA, such as UL144 or HVEM polypeptide variant as described herein.

BRIEF DESCRIPTION OF THE DRAWINGS

FIGS. 1A and 1B show traces of levels of binding of human HVEM Fc and human CMV UL144 Fc to human BTLA Fc, respectively. FIG. 1C shows traces of levels of binding of RhCMV UL144 Fc to human BTLA Fc.

FIGS. 5A-5B illustrate the activation of human peripheral blood cell subsets measured by CD69 (A) or CD107a (B) expression during a response to CMV infected NHDF cells following treatment with control Ig, UL144-Fc or HVEM-Fc. Freshly isolated PBMC cultured with mock- or CMV-infected NHDF cells were left untreated or were treated with HVEM-Fc, UL144-Fc, or human Ig control. FIG. 5A depicts graphs which indicate the percent of cells expressing CD69 within CD3+CD8+, CD3+CD4+, CD19+, CD56dim, CD56bright, or CD14+ gates over one week of culture. FIG. 5B depicts graphs which indicate the percent of cells expressing surface CD107a within CD56dim, CD56bright, and CD3+CD8+ cells following overnight culture. Results are representative of two separate experiments with at least 4 donors each. Graphs show mean+/−SEM, significant p values are shown.

FIG. 6A-6H are graphical representations depicting NK cell costimulation by HVEM-Fc correlates with expression of CD160. FIGS. 6A-6H illustrate the relative expression of CD160, BTLA, LIGHT, or HVEM in human peripheral blood cells (A-D), and correlations of CD56dim NK cell expression levels of these proteins and NKG2C and donor CMV seropositivity with the activation of NK cells by HVEM-Fc in the in vitro CMV response. Figures A-D are graphs which show MFI of BTLA (A), CD160 (B), HVEM (C), or LIGHT (D) in PBMC gated on CD14+, CD19+, CD3+CD4+, CD3+CD8+, CD56$^{dim}$ and CD56$^{bright}$. Data points represent individual donors. Enhancement of CD69 expression in NK cells by HVEM-Fc in FIG. 1A was calculated as the difference between CD69 expression in HVEM-Fc-treated and control-treated samples. FIGS. 6E-I are graphs showing correlations between enhanced CD69 and NK cell expression of CD160 (E), BTLA (F), LIGHT (G) and percent NKG2C+ (H). $R^2$ values for correlations are shown.

FIGS. 7A-B. Human BTLA- or CD160-expressing EL4 cells were stained with the indicated concentrations of HVEM-Fc or human CMV UL144 Fc. EC50 values calculated using four parameter (variable slope) analysis. FIG. 7C. Cells used above were stained with 20 µg/ml of wild-type, Y61A, or K64A HVEM-Fc. FIG. 7D. Cells used above were stained with 20 µg/ml of Fiala strain human CMV, G46K, or rhesus CMV UL144-Fc. FIG. 7E. Representative human CMV group UL144- or HVEM-expressing 293T cells were stained with 50 µg/ml of BTLA-Fc (white) or CD160-Fc (black). FIG. 7F. Human or rhesus BTLA- or CD160-expressing 293T cells were stained with 20 µg/ml of HVEM-Fc, human CMV UL144-Fc, or rhesus CMV UL144-Fc. Dot plots of GFP plotted against anti-human Fc show selective loss of interaction between CD160 and human CMV UL144.*No staining.

FIGS. 8A-B are graphs showing the induction of CD69 (A) and interferon gamma (B) in CD56dim, CD56bright, and CD8+ T cells following interleukin 2 stimulation of human peripheral blood cells treated with Ig control, UL144-Fc, or HVEM-Fc. Freshly isolated PBMC were treated with HVEM-Fc, UL144-Fc, or human Ig control and stimulated with 10 or 100 U/ml of IL-2. Graphs indicate the percent of cells expressing CD69 (A) or intracellular IFN-γ (B) within CD56$^{dim}$, CD56$^{bright}$ and CD3$^+$CD8$^+$ cells following overnight culture.

FIGS. 9A-F are histograms (A-B), and graphs (C-D) showing the induction of CD69, CD25 and CD107a in CD56dim and CD56 bright following interferon beta or interleukin 2 stimulation of purified NK cells treated with Ig control, UL144-Fc, or HVEM-Fc. The levels of cytokines produced in the cultures of stimulated NK cells are shown in graphs (E-F). Purified CD56$^+$ cells from whole blood were treated with HVEM-Fc, UL144-Fc or human Ig control and stimulated overnight with 20 U/ml of IFN-β (A, C, E) or 10 U/ml (B, D) or (F) of IL-2. Overlaid histograms of cells from a representative donor show CD56 plotted against CD69 (top row), CD25 (middle row), or CD107a (bottom row) (A-B). Graphs show the percent of CD56$^{dim}$ cells expressing CD69 (top row) CD25 (middle row) and CD 107a (bottom row) (C-D). Results are representative of two separate experiments with at least 4 donors each, mean+SEM. Culture supernatants were collected after three days of treatment and assayed for the presence of secreted cytokines (E-F). Levels of IFN-γ and IL-8 are shown for IFN-β and IL-2 stimulation, and levels of TNF-α and LT-α are shown for IL-2 stimulation. No TNF-α or LT-α was detected following TN-β treatment, and no IL-1-13, IL-2, IL-4, IL-5, IL-6, IL-10, or IL-12 p70 was detected following either stimulation. Graphs show mean+SEM, significant p values are shown.*none detected.

FIGS. 10A-10B are histograms of staining of NK92 cells with antibodies to BTLA (A) or CD160 (B.). Additional western blots shows interleukin 2 stimulation of NK92 cells treated with control Ig, HVEM-Fc, or UL144-Fc treatment (C), interleukin 2 stimulation of NK92 cells treated with control Ig or anti-BTLA (D), and interferon beta stimulation of NK92 cells treated with control Ig or anti-BTLA (E). The times of the stimulation are indicated above the blots, and the proteins blotted for are shown to the right of the blots. FIGS. 10A-B. NK92 cells were stained with anti-BTLA and anti-CD160. FIGS. 10C-E. NK92 cells were treated with the indicated Fc proteins or antibodies and stimulated with either 20 U/ml IL-2 (C), 2, 20, 200 U/ml IL-2 (D), or 1, 10, 100, and 1000 U/ml IFN-β (E) for the indicated times. Western blots show whole cell extracts of phospho-JAK1, phospho-STAT5, and phospho-AKT to monitor IL-2 signaling, or phospho-STAT1 to monitor IFN-β signaling, and STAT5 and actin to control for total protein levels.

FIG. 11A-11C are western blots showing stimulation of NK92 with K562 cells treated with control Ig, HVEM-Fc, or UL144-Fc treatment (A), stimulation of NK92 with K562 cells treated with control Ig, HVEM-Fc, or HVEM R109W-Fc treatment (B), and stimulation of NK92 with K562 cells transfected with control vector or HVEM (C). The times of the stimulation are indicated above the blots, and the proteins blotted for are shown to the right of the blots. FIGS. 11A-B. NK92 cells were treated with HVEM- or UL144-Fc (A) or HVEM-Fc or HVEM R109W-Fc (B) and stimulated with Imatinib treated K562 cells for the indicated times. FIG. 11C. NK92 cells were stimulated with Imatinib treated K562 cells transduced with GFP control- or HVEM-expressing vector for the indicated times. Western blots show whole cell extracts of phospho-ERK1/2 and phospho-AKT (S473) to monitor activation and total AKT and total ERK2 to control for total protein levels. K562 cells alone are shown to show target cell specific signals.

FIG. 12 is a tabular representation of relative binding of HVEM mutants to ligands. FIG. 12 shows a summary of the binding interactions between wild-type or 10 human HVEM proteins with BTLA, CD160 and LIGHT. The region of the amino acid substitution within HVEM is shown at the right of the table. Wild-type and mutant human HVEM were compared for the binding to human BTLA, CD160, and LIGHT. Mutations tested include P59S, G60D, Y61C, G72P, T82P, Ins92I, A102P, R109W, V215D, and G232S, all identified in follicular lymphoma and diffuse large B cell lymphoma.

FIG. 13 is histograms of cells transfected with wild-type or mutant HVEM stained with anti-HVEM. 293 cells were transduced with wild-type or mutant HVEM, or control vector and stained with anti-HVEM, and analyzed by flow cytometry.

FIG. 14 is graphs showing the relative binding of BTLA, CD160, or LIGHT titrated onto wild-type or mutant HVEM. 293 cells were transduced with wild-type or mutant human HVEM and stained with titrated human BTLA-Fc, CD160-Fc, LIGHT-FLAG to determine the impact of mutation on ligand binding.

FIG. 15A is a graph depicting binding data of BTLA binding to UL144 mutants expressed in 293 cells. FIG. 15B illustrates a 3-D structure of UL144 showing CRD1 and CRD2 binding domains which complex with BTLA. The position of these mutations is shown in FIG. 15B. The structural representation of the UL144 protein. FIG. 15C shows the alignment of the amino acid sequence of HVEM (SEQ ID NO: 80) and UL144 (SEQ ID NO: 81) as well as the consensus sequence (SEQ ID NO: 82). FIG. 15D is a series of graphs showing the relative expression of each of these UL144 mutants using antibody staining.

FIG. 16 is the amino acid sequence of wild-type HVEM (SEQ ID NO: 79).

FIG. 17 is a diagrammatic representation of showing the domains of wild-type HVEM with amino acid position 1 corresponding to amino acid position 39 of the wild-type sequence of SEQ ID NO: 79 (the signal sequence corresponding to amino acids 1 to 38 of SEQ ID NO: 79 is cleaved in the diagram of FIG. 16).

FIG. 18 is an illustration of the HVEM Network.

DETAILED DESCRIPTION

Figure 1:
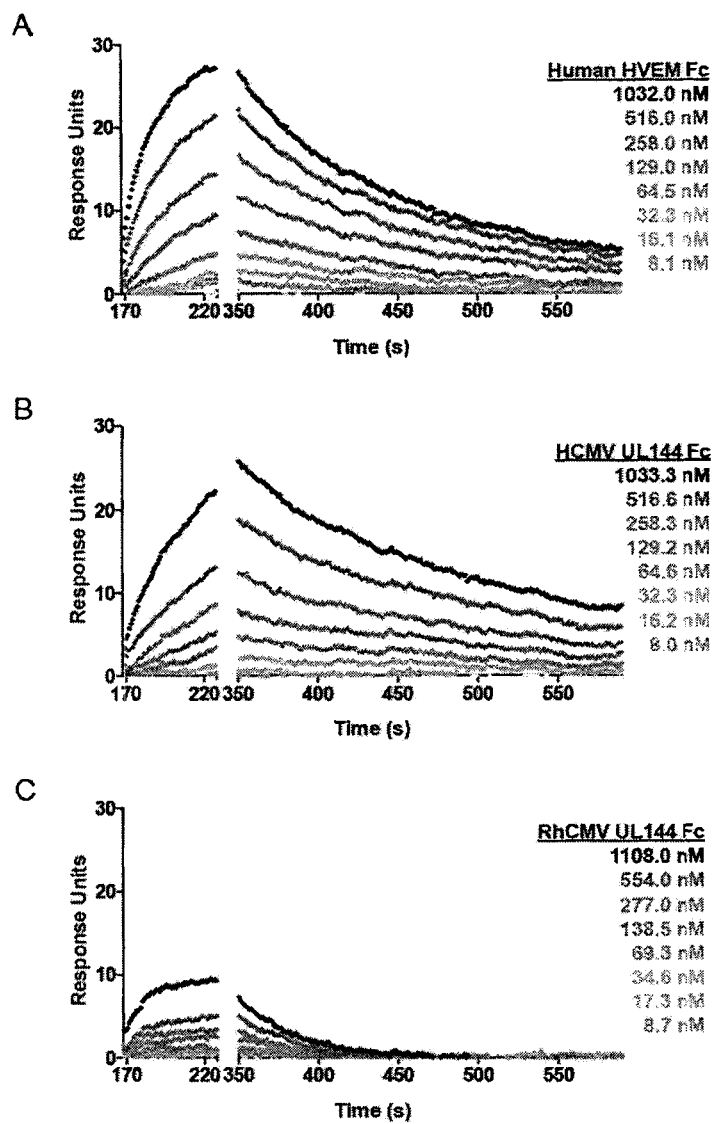
FIG. 1A-1C are graphical representations.

The present disclosure is based on the discovery that a viral homolog of HVEM, the Cytomegalovirus UL144 protein, has evolved specificity for BTLA without having specificity for CD160. This discovery allows for the ligand-specific HVEM polypeptide variants to be generated that bind to BTLA, but do not bind to CD160, as well as other HVEM ligands which provides suppression and inhibition of a proinflammatory response.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

In one aspect, the present disclosure provides an isolated HVEM polypeptide variant, wherein the variant binds to HVEM ligand BTLA and does not bind to HVEM ligand CD160. In certain embodiments, the variant does not bind to HVEM ligands LIGHT or LTα.

An illustration of the HVEM Network depicting the specificity of the ligands (upper panel) and cognate receptors (lower panel) is shown in FIG. 18. The arrows define the specific ligand-receptor interaction. The TNF related ligands are shown as trimers (unboxed). LTα is secreted as a homotrimer, and has modest affinity for HVEM (dashed line). The Ig superfamily members, BTLA and CD160, and herpes simplex virus (HSV) glycoprotein D (boxed) are ligands for HVEM. Human cytomegalovirus UL144, an HVEM ortholog, binds BTLA. Decoy receptor-3 (DcR3) binds LIGHT and the paralogous ligands, Fas Ligand and TL1a.

The term "wild-type HVEM protein" or "HVEM wild-type protein" refers to the Herpesvirus entry mediator protein (HVEM) protein having the amino acid sequence disclosed in EMBL-CDS: AAQ89238.1: *Homo sapiens* (human) HVEM as shown in FIG. 16 (SEQ ID NO: 79).

As used herein, a polypeptide "variant" or "derivative" refers to a polypeptide that is a mutagenized form of a polypeptide or one produced through recombination but that still retains one or more desired activities, such as the ability to bind to one specific ligand, but no longer retains another activity, such as the ability to bind to a second specific ligand.

The terms "HVEM polypeptide variant" or "HVEM variant" refer to an HVEM wild-type protein whose amino acid sequence is altered by one or more amino acids, such as by mutation, substitution or truncation. The HVEM variant may have conservative changes, wherein a substituted amino acid has similar structural or chemical properties, e.g., replacement of leucine with isoleucine. The HVEM variant may have nonconservative changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art, for example, DNAS-TAR™ software (DNASTAR Inc., Madison, Wis.). A variant of the invention will have functional properties as those with the illustrative HVEM R109W or HVEM P59S, for example.

"Isolated" or "purified" as those terms are used to refer to preparations made from biological cells or hosts means any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. Particularly for proteins, the procedures may include for example, but are not limited to, ammonium sulfate fractionation, gel filtration, ion exchange change chromatography, affinity chromatography, density gradient centrifugation, electrofocusing, chromatofocusing, and electrophoresis.

A preparation of DNA or protein that is "substantially pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

As used herein, the term "truncated", "truncation" or similar terminology refers to a HVEM polypeptide variant that contains less than the full amino acid sequence of a HVEM wild-type protein having a length of 283 amino acids as shown in FIG. 16 (SEQ ID NO: 79).

The term "ligand-specific HVEM variant" refers to an HVEM variant that binds to at least one HVEM ligand and does not bind to at least one other HVEM ligand.

The term "HVEM R109W" refers to an HVEM variant that contains a tryptophan residue instead of an arginine residue at amino acid position 109 of a wild-type HVEM protein.

The term "HVEM P59S" refers to an HVEM variant that contains a serine residue instead of a proline residue at amino acid position 59 of a wild-type HVEM protein.

The term "HVEM ligand" refers to a protein that binds to an HVEM wild-type and/or variant protein.

The term "UL144 protein" refers to the human cytomegalovirus UL144 protein.

The term "binds to" refers to a binding reaction that can be determinative of the presence of a protein in a heterogeneous population of proteins (e.g., a cell or tissue lysate) and other biologics. Thus, under standard conditions or assays used in binding assays, the specified polypeptide binds to a particular target molecule above background (e.g., 2×, 5×, 10× or more above background).

The term "suitable dimerization domain" includes, but is not limited to, a polypeptide domain that can associate with a second polypeptide domain to form a macromolecular complex.

The term "proinflammatory signaling pathway" refers to a biological pathway in a cell or tissue whose activation leads to an inflammatory response. In certain embodiments, a proinflammatory signaling pathway is in an immune cell or tissue. In certain embodiments, a proinflammatory signaling pathway is in a mucosal cell or tissue.

The term "inhibitory signaling pathway" refers to a biological pathway in a cell or tissue whose activation does not lead to or suppresses an inflammatory response. In certain embodiments, an inhibitory signaling pathway is in an immune cell or tissue. In certain embodiments, an inhibitory signaling pathway is in a mucosal cell or tissue.

The HVEM polypeptide variants of the present disclosure may include one or more mutations or substitutions as well as truncations as compared to wild-type HVEM protein. Reference herein to amino acid residues is made with respect to the full length HVEM wild-type protein as shown in FIG. 16 (see, also, Sequence Listing). HVEM wild-type protein includes several discrete functional domains as follows: signal peptide (residues 1-38), extracellular ligand binding domain (residues 39-202), transmembrane domain (203-223), and cytoplasmic topological domain (residues 224-283). The extracellular ligand binding domain (residues 39-202) includes four cysteine rich domains (CRDs) which define ligand specificity and are located as follows: CRD1 (residues 42-75), CRD2 (residues 78-119), CRD3 (residues 121-162) and CRD4 (residues 165-186).

It should also be recognized that reference is made herein to particular peptides beginning or ending at "about" a particular amino acid residue. The term "about" is used in this context because it is recognized that a HVEM polypeptide variant may be generated to include complete functional domains of the HVEM wild-type protein or portions thereof. Thus, a HVEM polypeptide variant may include one or a few, e.g., 2, 3 4 or 5 amino acids from the specified amino acid length. As such, reference, for example, to a HVEM polypeptide variant having an amino acid sequence of about amino acid residues 39 to 187 of SEQ ID NO: 79 would include an amino terminal peptide portion of HVEM excluding the complete signal peptide and include a carboxy terminus ending at amino acid residue 182 to amino acid residue 192, preferably at amino acid residue 187.

The HVEM polypeptide variants disclosed herein generally include all or a portion of the extracellular domain from about amino acid 39 to about amino acid 202 of SEQ ID NO: 79 and which retains BTLA binding activity but does not bind CD160. The variants may include one or more mutations or substitutions at amino acid residue position 59, 60, 61, 72, 82, 109, 232 of SEQ ID NO: 79, or any combination thereof. In various embodiments, the variant is a truncated wild-type HVEM variant having one or more mutations or substitutions at amino acid residue position 59, 60, 61, 72, 82, 109, 232 of SEQ ID NO: 79, or any combination thereof.

Truncated HVEM polypeptide variants generally include all or a portion of the extracellular ligand binding domain (residues 39-202) of HVEM wild-type protein. In various embodiments, the truncated variants may include all or a portion of CRD1; CRD1 and all or a portion of CRD2; CRD1, CRD2 and all or a portion of CRD3; CRD1, CRD2, CRD3 and all or a portion of CRD4; or alternatively all CRDs in their entireties, each of the variants having one or more mutations or substitutions. As such, in various embodiments, the variants of the present disclosure may include amino acid residues from about 39 to about 76, about 39 to about 98, about 39 to about 120, about 39 to about 141, about 39 to about 163, or about 39 to about 187 of SEQ ID NO: 79, and wherein the variant include at least one substitution or mutations and functionally retain BTLA binding activity but do not retains CD160 binding activity.

In one embodiment, the disclosure provides a HVEM polypeptide variant including CRD1 and CRD2 from about amino acid residue 39 to about residue 120 of SEQ ID NO: 79. The variant has decreased or no binding to CD160 while retaining BTLA binding, and is capable of delivering inhibitory signals to lymphocytes by avoiding activation signaling through CD160. In various embodiments, the variant further includes one or more an amino acid substitutions or mutations at residue position 59, 60, 61, 72, 82, 109 or any combination thereof. In some embodiments, the variant includes CRD1 and CRD2 from about amino acid residue 39 to about residue 120 of SEQ ID NO: 79 and further includes a mutation or substitution at either P59, R109 or both.

In one embodiment, the disclosure provides a HVEM polypeptide variant including CRD1, CRD2, and a portion of CRD3 from about amino acid residue 39 to about residue 141 of SEQ ID NO: 79. The variant has decreased or no binding to CD160 while retaining BTLA binding, and is capable of delivering inhibitory signals to lymphocytes by avoiding activation signaling through CD160. In various embodiments, the variant further includes one or more an amino acid substitutions or mutations at residue position 59, 60, 61, 72, 82, 109 or any combination thereof. In some embodiments, the variant includes CRD1, CRD2 and a portion of CRD3 from about amino acid residue 39 to about residue 141 of SEQ ID NO: 79 and further includes a mutation or substitution at either P59, R109 or both.

In various embodiments, the HVEM polypeptide variant of the present disclosure retains BTLA binding activity, but does not bind one or more of CD160, LIGHT, or LTα.

In one embodiment, the present disclosure provides an HVEM mutant R109W which has decreased or no binding to CD160 while retaining BTLA binding, and is capable of delivering inhibitory signals to lymphocytes by avoiding activation signaling through CD160.

The HVEM polypeptide variants of the present disclosure act like the viral protein in a broad spectrum of diseases, but, advantageously, without having antigenic properties of a foreign protein.

In other aspects the invention includes methods for making mutations or substitutions of HVEM used to discriminate between all of the HVEM ligands and multivalent forms of each of these HVEM variants, whereby the variants will have low antigenicity and can be used to target specific immune pathways in various diseases.

An HVEM Fc of the invention functions as a specific inhibitor of inflammatory processes and thus is used in a range of inflammatory conditions including but not limited to rheumatoid arthritis, lupus, Crohn's Disease, and similar autoimmune diseases. The present invention provides methods to expand the panel of mutant HVEM Fc proteins to create fully functional proteins capable of selectively binding either LIGHT, BTLA and CD160. TNFSF14 specific HVEM Fc blocks lung inflammation in an airway hyperresponsiveness model previously shown to be dependent on the activity of this ligand. BTLA specific HVEM Fc will be used as a broad spectrum inhibitory reagent with the capacity to inhibit T and B cell responses.

The present invention provides methods for CD160 specific HVEM to promote cytotoxic T cell and natural killer cell clearance of tumors in models of B cell lymphoma and melanoma. In several aspects of the invention, the present invention targets specific diseases in which each of the HVEM ligands has been shown to play a role. Additionally the present invention targets T cell and NK mediated immune disease in humans.

Current HVEM Fc reagents activate both positive and negative pathways by activating CD160 receptors on natural killer cells and cytotoxic T lymphocytes, and inhibitory BTLA receptors on these and other lymphocytes. The present invention provides a panel of mutated HVEM Fc reagents which can distinguish between different activating and inhibitory receptors, and methods of use of such reagents, allowing specific dampening of immune responses on these subsets where previous reagents have failed. Finally, present Fc fusion proteins are a proven technology in clinical use (Enbrel, etanercept), and while other Fc proteins target effector cytokines, the present invention provides methods to target effector cell subsets to regulate disease progression.

The present invention provides methods to identify mutations that distinguish between BTLA and CD160, and a panel of mutants that have high affinity ligand specific proteins. Another aspect of the present invention includes specific inhibition of B cells and NK cells using a viral variant of HVEM specific for BTLA. The present invention also includes activation of CD160 expressing NK cells using HVEM Fc.

The present invention provides a fusion protein of human IgG1 Fc with the cytomegalovirus protein UL144, which is specific for BTLA and which selectively activates inhibitory pathways in NK cells without activating CD160, and methods of using the same. The present invention also identifies a mutation in HVEM which selectively binds to BTLA, and a fusion protein with this mutant, and methods of using the same.

The present invention provides methods for the development of a BTLA-specific ligand constructed as a fusion protein with the ectodomain of human HVEM and Fc or other suitable dimerizing domain. The present invention provides methods for making HVEM specific mutants that, like UL144, are specific for BTLA. This molecule is significantly more efficacious at inhibiting T cell activation and innate cell activation than HVEM-Fc Modified HVEM-Fc represents a first-in-class drug as bio-modulator of inhibitory signaling.

In certain embodiments, an isolated HVEM variant, wherein the variant binds to BTLA and does not bind to CD160 is provided for. In certain embodiments, the variant does not bind to LIGHT.

In certain embodiments, the variant includes a wild-type HVEM protein or truncation thereof with an amino acid substitution at position 59, 60, 61, 72, 82, 109 and/or 232. In certain embodiments, the variant includes a wild-type HVEM protein or truncation thereof with an amino acid substitution at position 59. In certain embodiments, the variant includes a wild-type HVEM protein or truncation thereof with an amino acid substitution at position 60. In certain embodiments, the variant includes a wild-type HVEM protein or truncation thereof with an amino acid substitution at position 61. In certain embodiments, the variant includes a wild-type HVEM protein or truncation thereof with an amino acid substitution at position 72. In certain embodiments, the variant includes a wild-type HVEM protein or truncation thereof with an amino acid substitution at position 82. In certain embodiments, the variant includes a wild-type HVEM protein or truncation thereof with an amino acid substitution at position 109.

In certain embodiments, the variant includes all or a portion of the extracellular domain of HVEM-R109W. In certain embodiments, the variant includes all or a portion of the extracellular domain of HVEM-P59S. In certain embodiments, the variant includes the extracellular domain of UL144.

While the HVEM polypeptide variants of the present disclosure may be defined by exact sequence or motif sequences, one skilled in the art would understand that peptides that have similar sequences may have similar functions. Therefore, peptides having substantially the same sequence or having a sequence that is substantially identical or similar to HVEM polypeptide variants described herein are intended to be encompassed. As used herein, the term "substantially the same sequence" includes a peptide including a sequence that has at least 60+% (meaning sixty percent or more), preferably 70+%, more preferably 80+%, and most preferably 90+%, 95+%, or 98+% sequence identity with the HVEM polypeptide variant described herein which retains the same functional activity.

A further indication that two polypeptides are substantially identical is that one polypeptide is immunologically cross reactive with that of the second. Thus, a polypeptide is typically substantially identical to a second polypeptide, for example, where the two peptides differ only by conservative substitutions.

The term "conservative substitution" is used in reference to proteins or peptides to reflect amino acid substitutions that do not substantially alter the activity (for example, antimicrobial activity) of the molecule. Typically conservative amino acid substitutions involve substitution of one amino acid for another amino acid with similar chemical properties (for example, charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K) 5) Isoleucine (I), Leucine (L), Methionine (M), Valine (V); and 6) Phenylalanine (F), Tyrosine (Y), and Tryptophan (W).

The term "amino acid" is used in its broadest sense to include naturally occurring amino acids as well as non-naturally occurring amino acids including amino acid analogs. In view of this broad definition, one skilled in the art would know that reference herein to an amino acid includes, for example, naturally occurring proteogenic (L)-amino acids, (D)-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through a metabolic pathway.

The phrase "substantially identical," in the context of two polypeptides, refers to two or more sequences or subsequences that have at least 60+%, preferably 80+%, most preferably 90-95+% amino acid residue identity, when compared and aligned for maximum correspondence, as measured using a sequence comparison algorithm or by visual inspection.

As is generally known in the art, optimal alignment of sequences for comparison can be conducted, for example, by the local homology algorithm of Smith & Waterman ((1981) *Adv Appl Math* 2:482), by the homology alignment algorithm of Needleman & Wunsch ((1970) *J Mol Biol* 48:443), by the search for similarity method of Pearson & Lipman ((1988) *Proc Natl Acad Sci USA* 85:2444), by computerized implementations of these algorithms by visual inspection, or other effective methods.

HVEM polypeptide variants may have modified amino acid sequences or non-naturally occurring termini modifications. Modifications to the peptide sequence can include, for example, additions, deletions or substitutions of amino acids, provided the peptide produced by such modifications retains BTLA binding activity. Additionally, the peptides can be present in the formulation with free termini or with amino-protected (such as N-protected) and/or carboxy-protected (such as C-protected) termini Protecting groups include: (a) aromatic urethane-type protecting groups which include benzyloxycarbonyl, 2-chlorobenzyloxycarbonyl, 9-fluorenylmethyloxycarbonyl, isonicotinyloxycarbonyl and 4-methoxybenzyloxycarbonyl; (b) aliphatic urethane-type protecting groups which include t-butoxycarbonyl, t-amyloxycarbonyl, isopropyloxycarbonyl, 2-(4-biphenyl)-2-propyloxycarbonyl, allyloxycarbonyl and methylsulfonylethoxycarbonyl; (c) cycloalkyl urethane-type protecting groups which include adamantyloxycarbonyl, cyclopentyloxycarbonyl, cyclohexyloxycarbonyl and isobomyloxycarbonyl; (d) acyl protecting groups or sulfonyl protecting groups. Additional protecting groups include benzyloxycarbonyl, t-butoxycarbonyl, acetyl, 2-propylpentanoyl, 4-methylpentanoyl, t-butylacetyl, 3-cyclohexylpropionyl, n-butanesulfonyl, benzylsulfonyl, 4-methylbenzenesulfonyl, 2-naphthalenesulfonyl, 3-naphthalenesulfonyl and 1-camphorsulfonyl.

In various embodiments, HVEM polypeptide variants may be administered by any suitable means, including topical, parenteral, subcutaneous, intraperitoneal, intrapulmonary, intranasal, intravenous, and/or intralesional administration in order to treat the subject. However, in exemplary embodiments, the peptides are formulated for topical application, such as in the form of a liquid, cream, gel, ointment, foam spray or the like.

In certain embodiments, the variant includes a suitable dimerizing domain. In certain embodiments, the suitable dimerizing domain is an effectorless Fc domain of an Ig, such as human IgA, IgD, IgE, IgG, or IgM. In one embodiment, the Fc domain is IgG1 effectorless Fc domain.

In certain embodiments, binding of the variant to an HVEM ligand inhibits IL-2 signaling. In certain embodiments, binding of the variant to an HVEM ligand reduces expression of LT-β and interferon-γ.

In certain embodiments, a pharmaceutical composition comprising an isolated HVEM variant, wherein the variant binds to at least one ligand for HVEM and does not bind to at least one other ligand for HVEM, and a pharmaceutically acceptable carrier, is disclosed.

In another aspect, the present disclosure provides a pharmaceutical composition comprising an isolated HVEM polypeptide variant, wherein the variant binds to BTLA and does not bind to CD160 and optionally LIGHT and LTα, and a pharmaceutically acceptable carrier.

The term "pharmaceutical agent or drug" includes a chemical compound or composition capable of inducing a desired therapeutic effect when administered to a patient or subject.

The term "patient" or "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

In certain embodiments, a pharmaceutical composition includes a therapeutically effective amount of a ligand-specific HVEM polypeptide variant as described herein and a therapeutically effective amount of at least one additional therapeutic agent including, but not limited to, at least one other anti-inflammatory therapy agent.

In certain embodiments, a pharmaceutical composition includes a therapeutically effective amount of a ligand-specific HVEM polypeptide variant as described herein and a therapeutically effective amount of at least one additional therapeutic agent including, but not limited to, at least one other anti-inflammatory therapy agent.

The disclosure also provides a method for treating an inflammatory or auto-immune disease in a subject. The method includes administering to a subject a pharmaceutical composition including an isolated HVEM polypeptide variant, wherein the variant binds to at least one ligand for HVEM, such as BTLA, and does not bind to at least one other ligand for HVEM, such as CD160, and a pharmaceutically acceptable carrier.

In certain embodiments, a pharmaceutical composition includes a pharmaceutically acceptable diluent, carrier, solubilizer, emulsifier, preservative and/or adjuvant.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1990).

In certain embodiments, an effective amount of a pharmaceutical composition comprising a ligand-specific HVEM variant depends on the therapeutic context and objectives. One skilled in the art will appreciate that the appropriate dosage levels for treatment will vary depending in part on the molecule delivered, the indication for which the HVEM variant is being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

An inflammatory disease or condition includes a disease or condition that is characterized by the presence of an inflammatory response or the activation of a proinflammatory signaling pathway in a cell or tissue. In certain embodiments, a proinflammatory signaling pathway is in an immune cell or tissue. In certain embodiments, a disease is an inflammatory condition if (1) pathological findings associated with the disease or condition can be mimicked experimentally in animals by the activation of a proinflammatory signaling pathway in immune cells or tissues and/or (2) a pathology induced in experimental animal models of the disease or medical condition can be inhibited or abolished by treatment with agents that activate an inhibitory signaling pathway in immune cells or tissues.

In certain embodiments, an inflammatory disease or condition is selected from the group consisting of: rheumatoid arthritis, lupus, autoimmune diseases, Crohn's disease, ulcerative colitis, inflammatory bowel diseases, asthma, dermatitis, diverticulitis, pelvic inflammatory disease, atheroscloerosis, allergies, myopathies, and leukocyte defects. An inflammatory disease or condition may also include, but is no limited to, pruritus, skin inflammation, psoriasis, multiple sclerosis, rheumatoid arthritis, osteoarthritis, systemic lupus erythematosus, Hashimoto's thyroidis, myasthenia gravis, diabetes type I or II, asthma, inflammatory lung injury, inflammatory liver injury, inflammatory glomerular injury, atopic dermatitis, allergic contact dermatitis, irritant contact dermatitis, seborrhoeic dermatitis, Sjoegren's syndrome, keratoconjunctivitis, uveitis, inflammatory bowel disease, Crohn's disease, ulcerative colitis, an inflammatory disease of the joints, skin, or muscle, acute or chronic idiopathic inflammatory arthritis, myositis, a demyelinating disease, chronic obstructive pulmonary disease, interstitial lung disease, interstitial nephritis and chronic active hepatitis.

In another aspect, the disclosure provides a method of inhibiting a proinflammatory response in a subject comprising administering to the subject an agent which inhibits binding of herpesvirus entry mediator (HVEM) to CD160 or agonizes BTLA binding to HVEM. In various embodiments, the agent inhibits activation of natural killer (NK) cells and is a negative regulator of IL-2 signaling. In various embodiment, the agent is a polypeptide, antibody, or fragment thereof, UL144 or a HVEM polypeptide variant as described herein. In certain embodiments, the agent specifically inhibits binding of HVEM to CD160 without inhibiting binding of HVEM to BTLA, such as UL144 or a HVEM polypeptide variant as described herein.

The term "binds specifically" or "specific binding activity," when used in reference to an antibody means that an interaction of the antibody and a particular epitope has a dissociation constant of at least about $1\times10^{-6}$, generally at least about $1\times10^{-7}$, usually at least about $1\times10^{4}$, and particularly at least about $1\times10^{-9}$ or $1\times10^{-10}$ or less. As such, Fab, F(ab')$_2$, Fd and Fv fragments of an antibody that retain specific binding activity for an epitope of HVEM or CD160, are included within the definition of an antibody.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., Science 246:1275-1281 (1989), which is incorporated herein by reference). These and other methods of making, for example, chimeric, humanized, CDR-grafted, single chain, and bifunctional antibodies are well known to those skilled in the art (Winter and Harris, Immunol. Today 14:243-246, 1993; Ward et al., Nature 341:544-546, 1989; Harlow and Lane, Antibodies: A laboratory manual (Cold Spring Harbor Laboratory Press, 1988); Hilyard et al., Protein Engineering: A practical approach (IRL Press 1992); Borrabeck, Antibody Engineering, 2d ed. (Oxford University Press 1995); each of which is incorporated herein by reference).

Antibodies that bind specifically with HVEM or a HVEM ligand, such as CD160 can be raised using the receptor as an immunogen and removing antibodies that crossreact. An antibody of the invention conveniently can be raised using a peptide portion of HVEM or the HVEM ligand.

The disclosure also provides a method for treating cancer in a subject. The method includes administering to a subject a pharmaceutical composition including an isolated HVEM polypeptide variant, wherein the variant binds to at least one ligand for HVEM, such as BTLA, and does not bind to at least one other ligand for HVEM, such as CD160, and a pharmaceutically acceptable carrier.

Recent studies have shown that somatic mutations in HVEM (also known as TNFRSF14) either through deletion or nonsynonymous mutation are among the most common gene alterations in follicular and diffuse large B cell lymphoma. Follicular lymphoma harboring acquired TNFRSF14 mutations are associated with worse prognosis, highlighting the anti-inflammatory effect of HVEM in the tumor microenvironment. While the mechanism for the tumor suppressive role of HVEM is unclear, the absence of NK cell and cytotoxic T cell costimulation through CD160 may lead to aborted anti-tumor responses. Alternatively, the absence of HVEM would prevent inhibition of T cells expressing BTLA, thus promoting the release of B cell growth factors. Finally, the absence of HVEM may act in a cell intrinsic manner in tumor cells to prevent the initiation of death signals. Additionally, lymphoma bearing HVEM deletions would express BTLA alone and not in a complex with HVEM, and thus would be exposed to ligands from other cells, antibodies or biologics which could drive inhibitory signals to the tumor cell.

The term "cancer" as used herein, includes a variety of cancer types which are well known in the art, including but not limited to, dysplasias, hyperplasias, solid tumors and hematopoietic cancers. Many types of cancers are known to metastasize and shed circulating tumor cells or be metastatic, for example, a secondary cancer resulting from a primary cancer that has metastasized. Additional cancers may include, but are not limited to, the following organs or systems: brain, cardiac, lung, gastrointestinal, genitourinary tract, liver, bone, nervous system, gynecological, hematologic, skin, and adrenal glands. Additional types of cancer cells include gliomas (Schwannoma, glioblastoma, astrocytoma), neuroblastoma, pheochromocytoma, paraganlioma, meningioma, adrenalcortical carcinoma, medulloblastoma, rhabdomyoscarcoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia; and skin cancers including malignant melanoma, basal cell carcinoma, squamous cell carcinoma, Karposi's sarcoma, moles dysplastic nevi, lipoma, angioma, dermatofibroma, keloids, and psoriasis.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Regulation of NK Cells

Natural killer (NK) cells respond to IL-2 and IL-15 signaling by differentiating into fully functional effector cells that secrete antiviral cytokines required for host defense; however, the mechanisms regulating IL-2 receptor signaling by the host or pathogen remain unclear. It is demonstrated herein that the human cytomegalovirus or UL144 functions as a highly selective agonist of the inhibitory receptor, B and T lymphocyte attenuator (BTLA). UL144 binds exclusively to BTLA, subjecting NK cells to inhibitory signaling. Thus, UL144 engagement with BTLA dephosphorylates JAK1 and STAT5, decreasing the strength and duration of IL-2 receptor signaling, suppressing expression of antiviral cytokines interferon-γ and lymphotoxin-αβ. In contrast to UL144, its cellular ortholog herpesvirus entry mediator (HVEM) activates NK cell expression of IL-2Rα and CD69 via CD160. Taken together, the results reveal a novel mechanism by which BTLA limits IL-2 activation inhibiting the antiviral effector functions of NK cells, while HVEM-CD160 engagement promotes NK cell activation.

This example demonstrates that human CMV or UL144 is a specific agonist of inhibitory signaling through BTLA; UL144-BTLA inhibits IL-2 signaling resulting in diminished JAK1 phosphorylation; BTLA activation reduces NK cell expression of antiviral cytokines; and HVEM-CD160 activates NK cells.

The following experimental procedures were utilized.

Human peripheral blood cell isolation and activation.

Fresh human blood from normal healthy donors was mixed 1:1 with PBS and overlaid onto Ficoll (GE Healthcare, Uppsala, SE) for density gradient centrifugation. Peripheral blood mononuclear cells (PBMC) were isolated from buffy coats and washed twice with PBS. NK cells were further purified using EasySep Human NK Cell Enrichment Kit™ (Stemcell Technologies, Vancouver, Calif.) and confirmed to be >95% pure by CD56 staining. Cells resuspended to $1-2\times10^6$ cells per ml in R10 media (RPMI 1640 with 10% heat-inactivated fetal bovine serum, antibiotics, L-glutamine and 50 μM β-mercaptoethanol) were first incubated on ice 15-30 minutes with Fc fusion proteins or hIgG$_1$ control. For infectious co-culture experiments NHDF cells were infected with CMV at an MOI=1 for 6 hours, washed with PBS, and mixed with pretreated PBMC at a ratio of 100:1 (PBMC:NHDF). Alternatively, pretreated cells were then activated at 37° C. in flat-bottomed plates for the indicated times and concentrations of recombinant human IL-2 (rhIL-2, Biogen, Cambridge, Mass.) or recombinant human IFN-β (R & D systems, Minneapolis, Minn.).

Antibodies and Fc Fusion Proteins.

Antibodies used to identify PBMC populations include CD19 FITC, CD8 APC, CD4 eFluor 450, BTLA PE (eBioscience, San Diego, Calif.), CD3 PE-Alexa 610 (Invitrogen, Carlsbad, Calif.), CD69 PerCP-Cy5.5, CD160 Alexa 647 (Biolegend, San Diego, Calif.), CD25 PE, and CD56 Alexa-700 (BD Biosciences, San Diego, Calif.).

Purified fusion proteins of the extracellular domains of human BTLA, HVEM, human CMV UL144 and variants and rhesus CMV UL144 with human IgG$_1$ Fc were produced as previously described.

Phosphatidylinositol specific phospholipase C (PI-PLC) (Invitrogen, Carlsbad, Calif.) was used to distinguish between the glycophosphoinositide (GPI)-linked and transmembrane forms of CD160.

Cells and Surface Protein Expression.

EL4 and 293T cells were maintained in D10 media (DMEM with 10% heat-inactivated fetal bovine serum, antibiotics, L-glutamine and 50 μM β-mercaptoethanol). NK92 cells were maintained in NK92 media (RPMI 1640 with 12.5% heat-inactivated fetal bovine serum, 12.5% equine serum, antibiotics, L-glutamine and 50 μM β-mercaptoethanol) supplemented with 100 U/ml rhIL-2.

EL4 cells were transduced with human BTLA ires GFP (Watanabe et al., *Nat Immunol* 4:670-679 (2003)) or human CD160 (Open Biosystems, Huntsville, Ala.) cloned into ires GFP retroviral plasmid by PCR amplification. Pseudotyped single infection retrovirus was produced by cotransfection of retroviral plasmid, pCG VSVg envelope protein, and Hit60 gag-pol as previously described (Sedy et al., *Nat Immunol* 6:90-98 (2005)). EL4 cells were sorted for GFP expression to increase the frequency of BTLA and CD160 expressing cells. 293T cells were transduced with UL144 derived from human CMV strains cloned in pND vector (Cheung et al. *J Biol Chem* 280:39553-39561 (2005)) by calcium phosphate transfection. UL144 mutants were produced by site-directed mutagenesis. 293T cells were transduced with human BTLA or CD160 as described above, or with de novo synthesized rhesus BTLA or CD160 (Mr. Gene, Regensburg, Del.) cloned into ires GFP retroviral plasmid by PCR amplification. BTLA mutants were produced by round-the-world PCR. 293T cells were used for experiments coexpressing BTLA and UL144 using the vectors described above, and BTLA and human HVEM in pcDNA3 (Cheung et al. *J Biol Chem* 280:39553-39561 (2005)). All oligonucleotides used for PCR amplification and site-directed mutagenesis are listed in Table 1.

TABLE 1

Primers used for cloning and site directed mutagenesis.

| Gene | Primer | Sequence |
|---|---|---|
| Human CD160 | | |
| Cloning | hCD1605BglII | AGTCAGATCTGCGTGCAGGA TGCTGTTG (SEQ ID NO: 1) |
| Cloning | hCD1603XhoI | AGTCCTCGAGGGCTTACAAAG CTTGAAGGG (SEQ ID NO: 2) |
| Rhesus BTLA | | |
| Cloning | RhBTLA BglII | AGTCAGATCTGTGCAGGAAAT GAAGACATTG (SEQ ID NO: 3) |
| Cloning | RhBTLA XhoI | AGTCCTCGAGTCAGAAACAGA CTTAACTCCTCACAC (SEQ ID NO: 4) |
| Rhesus CD160 | | |
| Cloning | RhCD160 BglII | AGCTAGATCTGCGTGCAGGAT GCTGATG (SEQ ID NO: 5) |
| Cloning | RhCD160 XhoI | AGTCCTCGAGAAGGCTTACA AAGCTTGAAGGACC (SEQ ID NO: 6) |
| Human CMV UL144 | | |
| E27A Mutant For | Fiala UL144 E46 | AAACCCGAAGCAGTGCANIT AGGAAATCAGTG (SEQ ID NO: 7) |
| E27A Mutant Rev | Fiala UL144 E46 | TAATTGCACTGCTTCGGGTTT GCATATTTCAG (SEQ ID NO: 8) |
| Q33A Mutant For | Fiala UL144 Q52 | TTAGGAAATGCGTGTTGTCCC CCATGTAAACAAG (SEQ ID NO: 9) |
| Q33A Mutant For | Fiala UL144 Q52 | GGGACAACACGCATTTCCTAA TTGCACTTCTTC (SEQ ID NO: 10) |
| P36A Mutant For | Fiala UL144 P55 | CAGTGTTGTGCCCCATGTAAA CAAGGATATCGTG (SEQ ID NO: 11) |
| P36A Mutant For | Fiala UL144 P55 | TTTACATGGGGCACAACACTG ATTTCCTAATTG (SEQ ID NO: 12) |
| G41A Mutant For | Fiala UL144 G60 | TGTAAACAAGCATATCGTGTT ACAGGACAATGTAC (SEQ ID NO: 13) |
| G41A Mutant For | Fiala UL144 G60 | AACACGATATGCTTGTTTACA TGGGGACAACACTG (SEQ ID NO: 14) |

TABLE 1-continued

Primers used for cloning and site directed mutagenesis.

| Gene | Primer | Sequence |
| --- | --- | --- |
| Y42A Mutant | UL144F-Y42A-F | CCCCCATGTAAACAAGGAGCT CGTGTTACAGGACAATG (SEQ ID NO: 15) |
| Y42A Mutant | UL144F-Y42A-R | CATTGTCCTGTAACACGAGCTC CTTGTTTACATGGGGG (SEQ ID NO: 16) |
| R43A Mutant | Fiala UL144 R62A For | CAAGGATATGCTGTTACAGGAC AATGTACGCAATATAC (SEQ ID NO: 17) |
| R43A Mutant | Fiala UL144 R62A For | TCCTGTAACAGCATATCCTTGTT TACATGGGGG (SEQ ID NO: 18) |
| T45A Mutant | Fiala UL144 T64 For | TATCGTGTTGCAGGACAATGTAC GCAATATACG (SEQ ID NO: 19) |
| T45A Mutant | Fiala UL144 T64 For | ACATTGTCCTGCAACACGATATC CTTGTTTACATGG (SEQ ID NO: 20) |
| G46A Mutant | Fiala UL144 G65 For | CGTGTTACAGCACAATGTACGCA ATATACGAGTAC (SEQ ID NO: 21) |
| G46A Mutant | Fiala UL144 G65 Rev | CGTACATTGTGCTGTAACACGAT ATCCTTGTTTAC (SEQ ID NO: 22) |
| G46K Mutant | FUL144-G46K 5' | AAACAAGGATATCGTGTTACAAA ACAATGTACGCAATATACGAGT (SEQ ID NO: 23) |
| G46K Mutant | FUL144-G46K 3' | ACTCGTATATTGCGTACATTGTTTT GTAACACGATATCCTTGTTT (SEQ ID NO: 24) |
| Q50A Mutant | Fiala UL144 Q69 For | CAATGTACGGCATATACGAGTACA ACATGTACAG (SEQ ID NO: 25) |
| Q50A Mutant | Fiala UL144 Q69 Rev | ACTCGTATATGCCGTACATTGTCCT GTAACACGATATC (SEQ ID NO: 26) |
| T52A Mutant | Fiala UL144 T71 For | ACGCAATATGCGAGTACAACATGT ACACTTTGCCC (SEQ ID NO: 27) |
| T52A Mutant | Fiala UL144 T71 Rev | TGTTGTACTCGCATATTGCGTACAT TGTTCTGTAAC (SEQ ID NO: 28) |
| L68A Mutant | Fiala UL144 L86 For | GTATCAGGGGCTTACAATTGTACC AATTGCACTG (SEQ ID NO: 29) |
| L68A Mutant | Fiala UL144 L86 Rev | ACAATTGTAAGCCCCTGATACATAC GTACCGTTAG (SEQ ID NO: 30) |
| P106A Mutant | Fiala UL144 P124 For | TTTTCCGTTGCAGGCGTCCAACATC ACAAGCAACG (SEQ ID NO: 31) |
| P106A Mutant | Fiala UL144 P124 Rev | TTGGACGCCTGCAACGGAAAATGA CGTATAATTC (SEQ ID NO: 32) |

Human BTLA

| Q37A Mutant | HuBTLAQ37Atop | CATGTGATGTAGCGCTTTATATA AAGAGACAATCTGAACACTC (SEQ ID NO: 33) |
| --- | --- | --- |
| Q37A Mutant | HuBTLAQ37Abot | CTTTATATAAAGCGCTACATCACA TGATTCTTTCCCATG (SEQ ID NO: 34) |
| L38H Mutant | HuBTLAL38Htop | ATGTGATGTACAGCATTATATAAGA GACAATCTGAACACTCC (SEQ ID NO: 35) |
| L38H Mutant | HuBTLAL38Hbot | TTGTCTCTTTATATAATGCTGTACATC ACATGATTCTTTCC (SEQ ID NO: 36) |
| R42D Mutant | HuBTLAR42Dtop | CTTTATATAAAGGACCAATCTGAACAC TCCATCTTAGC (SEQ ID NO: 37) |
| R42D Mutant | HuBTLAR42Dbot | GTGTTCAGATTGGTCCTTTATATAAAG CTGTACATCACATGATTC (SEQ ID NO: 38) |
| E45A Mutant | HuBTLAE45Atop | AGAGACAATCTGCACACTCCATCTTAG CAGGAGATCC (SEQ ID NO: 39) |
| E45A Mutant | HuBTLAE45Abot | AAGATGGAGTGTGGAGATTGTCTCTTT ATATAAAGCTGTAC (SEQ ID NO: 40) |
| E57A Mutant | HuBTLAE57Atop | CTTTGAACTAGCATGCCCTGTGAAATA CTGTGCTAAC (SEQ ID NO: 41) |
| E57A Mutant | HuBTLAE57Abot | TCACAGGGCATGCTAGTTCAAAGGGAT CTCCTGCTAAG (SEQ ID NO: 42) |
| P59A Mutant | HuBTLAP59Atop | GAACTAGAATGCGCTGTGAAATACTGT GCTAACAGGC (SEQ ID NO: 43) |
| P59A Mutant | HuBTLAP59Abot | GTATTTCACAGCGCATTCTAGTTCAA AGGGATCTC (SEQ ID NO: 44) |
| K90A Mutant | HuBTLAK90Atop | ACAAGTTGGCGGAAGAGAAGAACA TTTCATTTTTCATTC (SEQ ID NO: 45) |
| K90A Mutant | HuBTLAK90Abot | CTTCTCTTCCGCCCAACTTGTTTGTCT ATCTTCAAGTTTTAC (SEQ ID NO: 46) |
| V117A Mutant | HuBTLAV117Atop | TGTTCTGCAAATTTTCAGTCTAATCTC ATTGAAAGC (SEQ ID NO: 47) |
| V117A Mutant | HuBTLAV117Abot | GATTAGACTGAAAATTTGCAGAACAG CGGTATGACCC (SEQ ID NO: 48) |
| N118F Mutant | HuBLTAN118Ftop | GCTGTTCTGCATTTTTTCAGTCTAATCT CATTGAAAGC (SEQ ID NO: 49) |
| N118F Mutant | HuBTLAN118Fbot | TAGACTGAAAAAATGCAGAACAGCGG TATGAC (SEQ ID NO: 50) |

TABLE 1-continued

Primers used for cloning and site directed mutagenesis.

| Gene | Primer | Sequence |
| --- | --- | --- |
| F119A Mutant | HuBTLAF119Atop | GTTCTGCAAATGCTCAGTCTAATCTCA TTGAAAGCCAC (SEQ ID NO: 51) |
| F119A Mutant | HuBTLAF119Abot | GAGATTAGACTGAGCATTTGCAGAAC AGCGGTATG (SEQ ID NO: 52) |
| S121H Mutant | HuBTLAS121Htop | CAAATTTTCAGCATAATCTCATTGAAA GCCACTCAAC (SEQ ID NO: 53) |
| S121H Mutant | HuBTLAS121Hbot | CAATGAGATTATGCTGAAAATTTGCAG AACAGCG (SEQ ID NO: 54) |
| H127D Mutant | HuBTLAH127Dtop | CATTGAAAGCGACTCAACAACTCTTTA TGTGACAGATG (SEQ ID NO: 55) |
| H127D Mutant | HuBTLAH127Dbot | GTTGTTGAGTCGCTTTCAATGAGATTA GACTGAAAATTTG (SEQ ID NO: 56) |
| S128H Mutant | HuBTLAS128Htop | TGAAAGCCACCATACAACTCTTTATGT GACAGATGTAAAAAG (SEQ ID NO: 57) |
| S128H Mutant | HuBTLAS128Hbot | AAGAGTTGTATGGTGGCTTTCAATGAG ATTAGACTG (SEQ ID NO: 58) |

Binding Assays

Flow cytometric binding assays were performed as previously described (Cheung et al. *J Biol Chem* 280:39553-39561 (2005)). Cells were incubated with Fc ligands for 30 minutes at 4° C. in buffer (PBS with 2% FBS), washed twice and incubated with donkey anti-human Fc APC (Jackson Immunoresearch, West Grove, Pa.) for 15 minutes at 4° C. in buffer, washed twice and analyzed. Specific mean fluorescence intensity (MFI) was calculated by subtracting experimental cellular MFI from control cellular MFI.

BTLA Mutagenesis and Epitope Mapping

Anti-human BTLA used for epitope mapping include J168 (BD Biosciences, San Diego, Calif.), MIH26 (eBioscience, San Diego, Calif.), and monoclonal (6F4) and polyclonal rat anti-human BTLA produced as previously described (Cheung et al., *J Immunol* 183:7286-7296 (2009)). These were detected by goat anti-mouse APC (BD Bioscience, San Diego, Calif.) and donkey anti-rat APC (Jackson Immunoresearch, West Grove, Pa.).

Surface Plasmon Resonance Kinetic Affinity Measurement

Human BTLA Fc ligand was immobilized onto a CM5 sensor chip to 150 relative units using amine coupling. Sensograms were collected at 25° C. at a flow rate of 30 µl/min, and specific binding was determined by subtraction of control from ligand channels. Indicated concentrations of analyte were injected from vials cooled to 7° C. Data collection included 90 µl of analyte for 3 minutes followed by disassociation for 15 minutes. The sensor surface was regenerated after each cycle with a 30 second pulse of 15 µl 10 mM Glycine pH 2.5. Affinity measurements were made by analyzing both the first 10 seconds following analyte injection and disassociation using the kinetic analysis module of the BIAevaluation™ software (version 4.1) with both the Langmuir and the Bivalent fit models.

Western Analysis

NK92 cells used for IL-2 activation were first resuspended in NK92 media without IL-2 overnight followed by resuspension in serum-free media for at least 4 hours. These cells were then washed and resuspended in PBS and preincubated with Fc fusion proteins similar to human cell experiments outlined above. Preincubated cells were aliquoted to 0.5-1×10$^6$ cells per condition were activated at 37° C. with the indicated concentrations of rhIL-2 and for the indicated times. Activation reactions were quenched with ice cold PBS and lysed in RIPA buffer at 4° C. for 20 minutes and centrifuged at 14,000 rpm, 4° C. Extracts were boiled in SDS loading buffer containing 1% β-mercaptoethanol for 5 minutes and resolved by SDS-PAGE on 10% Bis-Tris gels (Invitrogen, Carlsbad, Calif.). Proteins were transferred using tank method to PVDF membrane and blocked with 1% ovalbumin in TBS-T buffer, and blotted with either phospho-JAK1, phospho-AKT (S473), phospho-extracellular-signal regulated kinase (ERK) ½, total AKT (Cell Signaling, Danvers, Mass.), phospho-signal-transducer and activator of transcription (STAT) 5a/b (Millipore, Temecula, Calif.), total JAK1, total ERK2 (Santa Cruz, Santa Cruz, Calif.), or total actin followed by anti-rabbit HRP (GE Healthcare), anti-mouse HRP, or anti-mouse AP (Santa Cruz, Santa Cruz, Calif.), and visualized by enhanced chemiluminescence (Thermo Scientific, Rockford, Ill.) or by BCIP®/NBT substrate deposition (Sigma-Aldrich, Saint Louis, Mo.).

Quantitative RT-PCR Analysis

Human NK cells stimulated with IL-2 and UL144-Fc were first washed with PBS and then RNA was harvested using RNeasy® Mini kit (Qiagen, Valencia, Calif.). cDNA was transcribed from RNA using the iScript™ cDNA Synthesis kit (Bio-Rad, Hercules, Calif.). Transcripts were amplified in 10 µl volume using 300 nM of primers in Power SYBR® Green PCR Master Mix on an ABI 7900HT Real-Time PCR System and specific products were analyzed using SDS v2.3 (Life Technologies, Carlsbad, Calif.). Primers used for quantitative RT-PCR analysis are shown in Table 2.

TABLE 2

Primers used for quantitative RT-PCR.

| Gene | Primer | Sequence |
| --- | --- | --- |
| | | LTA |
| Forward | Lta F | ACTACCGCCCAGCAGTGT (SEQ ID NO: 59) |
| Reverse | Lta R | GTGTCATGGGGAGAACCAA (SEQ ID NO: 60) |

TABLE 2-continued

Primers used for quantitative RT-PCR.

| Gene | Primer | Sequence |
|---|---|---|
| LTB | | |
| Forward | Ltb F | GGCGGTGCCTATCACTGT (SEQ ID NO: 61) |
| Reverse | Ltb R | TTCTGAAACCCCAGTCCTTG (SEQ ID NO: 62) |
| LIGHT | | |
| Forward | L Fwd QPCR SS | TCTCTTGCTGTTGCTGATGG (SEQ ID NO: 63) |
| Reverse | L Rev QPCR SS | CTCGTGAGACCTTCGCTCTT (SEQ ID NO: 64) |
| TNF | | |
| Forward | Tnfa F | CAGCCTCTTCTCCTTCCTGAT (SEQ ID NO: 65) |
| Reverse | Tnfa R | GCCAGAGGGCTGATTAGAGA (SEQ ID NO: 66) |
| TNFRSF14 | | |
| Forward | HuHVEM RTP (+) | AGCAGCTCCCCACTGGGTATG (SEQ ID NO: 67) |
| Reverse | HuHVEM RTP (−) | GATTAGGCCAACTGTGGAGCA (SEQ ID NO: 68) |
| BTLA | | |
| Forward | hBTLA Frwd | GCCTCTACTCATCACTACCTGTTTTC (SEQ ID NO: 69) |
| Reverse | hBTLA Rev | TCAGAGAGTTCATTTTGCTTTCC (SEQ ID NO: 70) |
| CD160 | | |
| Forward | HuCD160For | CCTCACTACATCCGTGAACTCC (SEQ ID NO: 71) |
| Reverse | HuCD160Rev | CTGCTGGTATCCTTGGCTTC (SEQ ID NO: 72) |
| SOCS1 | | |
| Forward | SOCS1 Fwd | CCCCTGGTTGTTGTAGCAG (SEQ ID NO: 73) |
| Reverse | SOCS1 Rev | GTAGGAGGTGCGAGTTCAGG (SEQ ID NO: 74) |
| SOCS3 | | |
| Forward | SOCS3 Fwd | CTTCGACTGCGTGCTCAAG (SEQ ID NO: 75) |
| Reverse | SOCS3 Rev | GTAGGTGGCGAGGGGAAG (SEQ ID NO: 76) |
| L32 | | |
| Forward | L32 F | GGATCTGGCCCTTGAACCTT (SEQ ID NO: 77) |
| Reverse | L32 R | GAAACTGGCGGAAACCCA (SEQ ID NO: 78) |

The following experimental results were observed.

HVEM and UL144 Bind BTLA with Similar Affinity.

Two-fold dilutions of human HVEM Fc human CMV UL144 Fc were injected over human BTLA Fc immobilized to dextran sulfate and a control channel in replicate at the indicated concentrations. Representative traces of the first minute following injection and 4 minutes of dissociation of the analyte are shown. $K_D$ was calculated from modeling both a 1:1 and 1:2 fit. Rate constants calculated using a 1:2 model of ligand to analyte binding showed very low secondary $k_{on}/k_{off}$ rate constants for both human and rhesus CMV UL144, indicating that UL144 may preferentially bind BTLA as a monomer HVEM and UL144 Bind the Same Surface of BTLA.

EL4 cells transduced with wild-type or mutant human BTLA were stained with 10 μg/ml of HVEM Fc or human CMV UL144 Fc or with polyclonal or monoclonal antibodies specific for human BTLA as indicated. Fusion proteins were detected with anti-human Fc and anti-BTLA was detected with anti-rat (6F4) or anti-mouse (J168, MIH26). From top to bottom graphs are specific MFI staining of HVEM Fc, UL144 Fc, J168 anti-BTLA, 6F4 anti-BTLA, and either polyclonal anti-BTLA (FIG. 2A) or MIH26 anti-BTLA (FIG. 2B) staining on cells within the GFP+ gate showing that both HVEM Fc and human CMV UL144 Fc use residues Q37, R42, P59 and H127 but not E45, E57, N118, F119 and S121, that residue R42 is required to bind anti-human BTLA J168, and that residue E57 is required to bind anti-human BTLA MIH26. The K90A mutation results in poor protein expression. In FIG. 2C the structure of BTLA is shown complexed to HVEM (top) and rotated 90° about the y-axis complexed with a second BTLA Ig molecule (bottom). (Protein Data Bank ID code 2AW2, Structures visualized using The PyMOL Molecular Graphics System, Version 0.99rc6, Schrödinger, LLC.) The surface of BTLA is shown in gray together with either HVEM (magenta) or a second BTLA Ig domain (light blue) as a main chain backbone with BTLA surface mutations indicated as shown. BTLA residues Q37, R42, P59 and H127 that are required for optimal binding of HVEM and UL144 are colored dark red. Residues E45 and E57 localized within the putative BTLA dimerization surface are colored orange. Residues N118, F119, and S121 located within the F-G loop of the BTLA Ig domain are colored teal. Residue K90 that is required for optimal surface expression is colored yellow.

BTLA Complexes in Cis Prevent Binding to HVEM and UL144 Fc.

Figure 3:
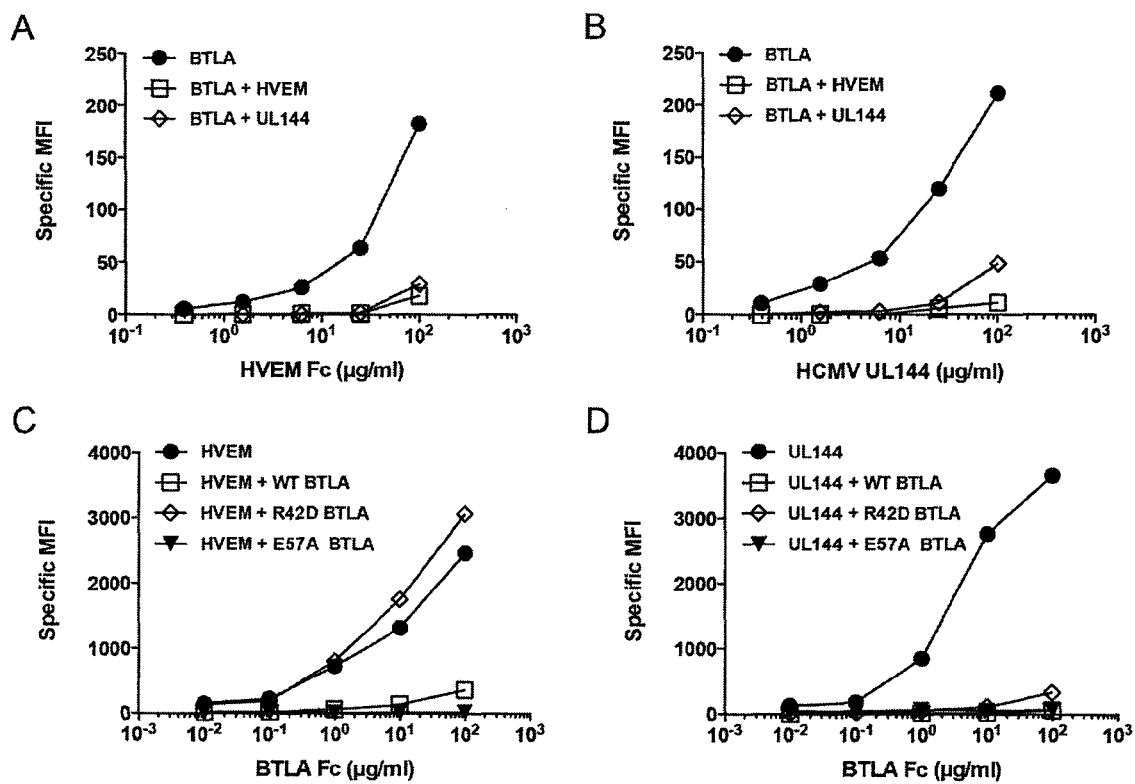
FIGS. 3A-3D are graphs depicting levels of staining with HVEM Fc (A) or human CMV UL144 Fc (B) of 293T cells transfected with BTLA alone or with HVEM or human CMV UL 144, and staining with BTLA Fc of 293T cells transfected with HVEM (C) or human CMV UL144 (D) alone or with wild-type, R42D, or E57A BTLA.

293T cells transfected with BTLA alone or together with HVEM or human CMV UL144 were stained with the indicated concentrations of HVEM Fc (FIG. 3A) or human CMV UL144 Fc (FIG. 3B). Binding curves show a specific block of HVEM Fc or human CMV UL144 Fc binding to BTLA when either HVEM or human CMV UL144 is coexpressed. 293T cells transfected with HVEM (FIG. 3C) or human CMV UL144 (FIG. 3D) alone or together with wild-type, R42D, or E57A BTLA were stained with the indicated concentrations of BTLA Fc. Binding curves show a specific block of BTLA Fc binding to HVEM or human CMV UL144 when wild-type BTLA is coexpressed, that is reversed only when the R42D mutant is coexpressed with HVEM and not with human CMV UL144.

HVEM but not Human CMV UL144 Binds to Human CD160.

Figure 4:
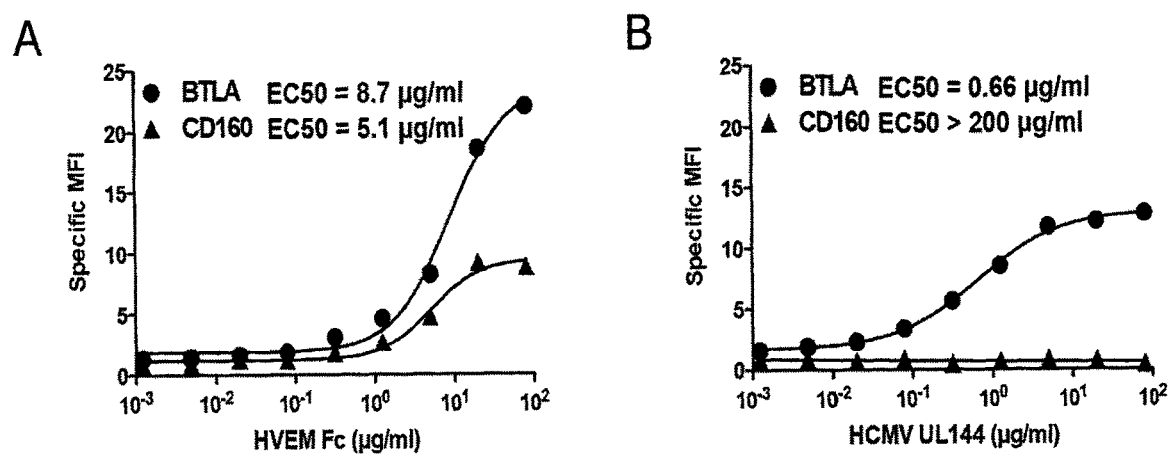
FIGS. 4A and 4B are graphical representations depicting levels of staining with the indicated concentrations of HVEM-Fc (A) or human CMV UL144 Fc (B) of EL4 cells expressing human BTLA or human CD160 respectively.

To address whether UL144 binds CD160, saturating binding of HVEM-Fc to cells expressing human BTLA or CD160 was measured and similar disassociation constants were found (FIG. 4A). UL144-Fc also bound cells expressing BTLA, but failed to bind to CD160 (FIG. 4B). EL4 cells expressing human BTLA or human CD160 were stained with the indicated concentrations of HVEM-Fc (FIG. 4A) or human CMV UL144 Fc (FIG. 4B). Binding curves show specific binding of HVEM-Fc to BTLA and CD160, while human CMV UL144 binds only to BTLA. EC50 values were calculated using the nonlinear regression four parameter (variable slope) analysis module of GraphPad Prism™ software (version 5.0b).

HVEM-Fc Co-Stimulates NK Responses to CMV

Figure 7:
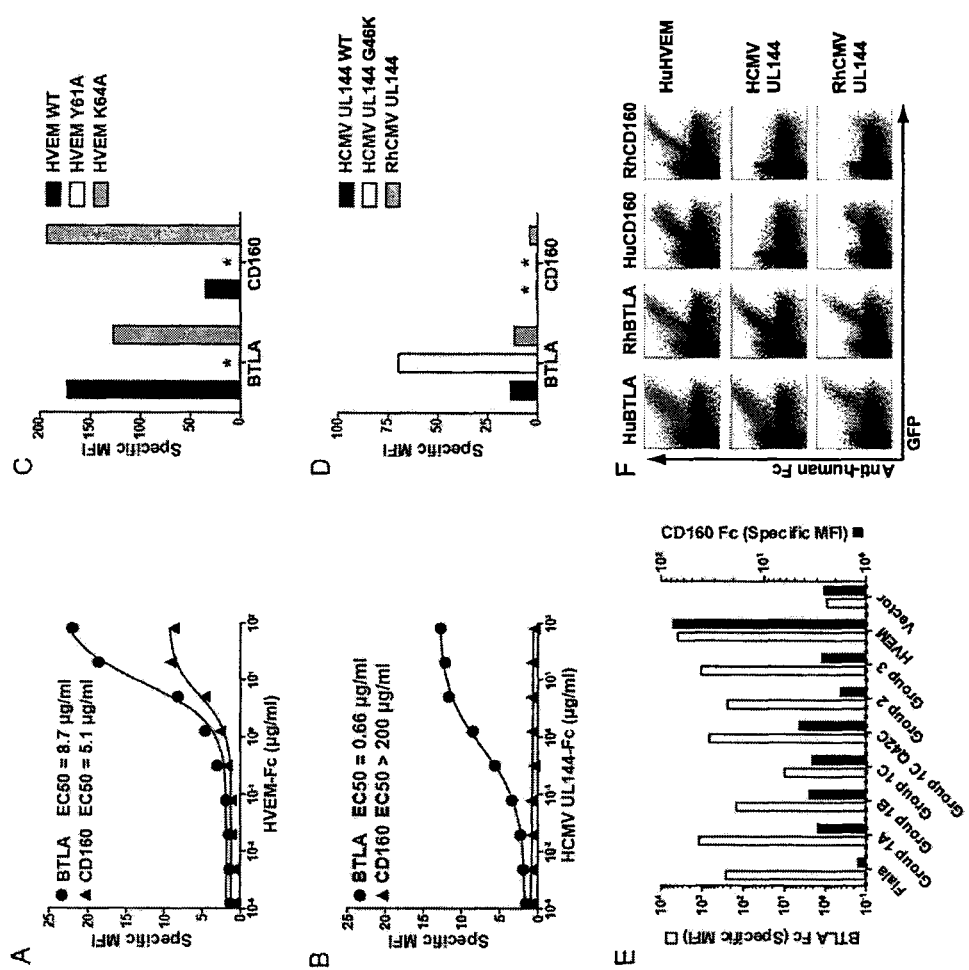
FIGS. 7A-7F are graphical representations depicting UL144 binding restricted to BTLA.

To test how HVEM and its viral ortholog UL144 function to regulate immune responses during viral infection, expression of activation markers in cells from human peripheral blood mixed with CMV infected fibroblasts was monitored (FIG. 7). All subsets of PBMC induced CMV-dependent expression of CD69 that steadily increased throughout the duration of the co-cultures. However, unique enhancement of CD69 expression in $CD56^{dim}$ NK cells at days 1 and 3 in PBMC treated with HVEM-Fc (FIG. 5A) was observed. A similar enhancement of CD107a expression in $CD56^{dim}$ NK cells after one day of culture (FIG. 5B) was observed. Thus, HVEM-Fc specifically enhances early activation of $CD56^{dim}$ NK cells during responses to CMV.

CMV Induced NK Cell Activation Correlates with CD160 Expression.

Figure 6:
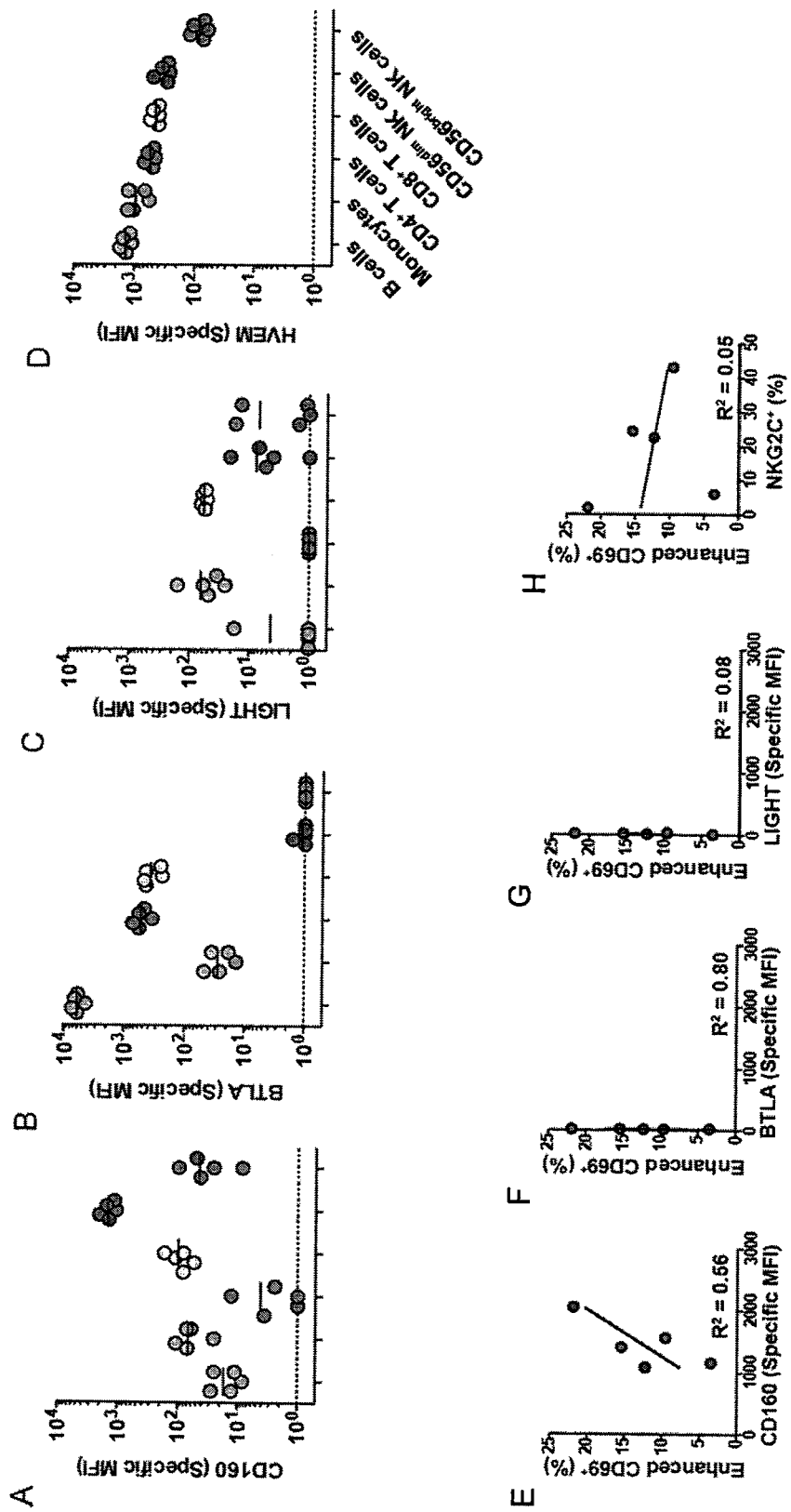

To identify which HVEM or UL144 ligands were present in lymphocytes, human peripheral blood was examined for BTLA, CD160, HVEM and LIGHT expression. BTLA and CD160 expression was inversely correlated on most PBMC subsets, while HVEM was broadly expressed by all PBMC and LIGHT showed specific expression in monocytes, $CD8^+$ T cells and weak expression in NK cells (FIG. 6A-D). In particular, B cells showed the highest BTLA expression and among the lowest CD160 expression. In contrast $CD56^{dim}$ NK cells showed the highest CD160 expression and among the lowest BTLA expression. T cells and monocytes expressed intermediate levels of BTLA and CD160, while $CD56^{bright}$ NK cells expressed low levels of both BTLA and CD160. The expression of HVEM ligands was compared to the increased CD69 percent co-stimulated by HVEM-Fc (FIG. 6E-G). Co-stimulation by HVEM-Fc was most associated with $CD56^{dim}$ NK cell CD160, while BTLA and LIGHT were expressed at very low levels. Additionally, co-stimulation by HVEM-Fc was not associated with the percent of NK cells expressing NKG2C, or CMV seropositivity of the donors (FIG. 6H), indicating that HVEM co-stimulation was independent of the donor CMV infectious status but did correlate with CD160 levels in $CD56^{dim}$ NK cells.

Human CMV UL144 Binds BTLA but not CD160.

Figure 2:
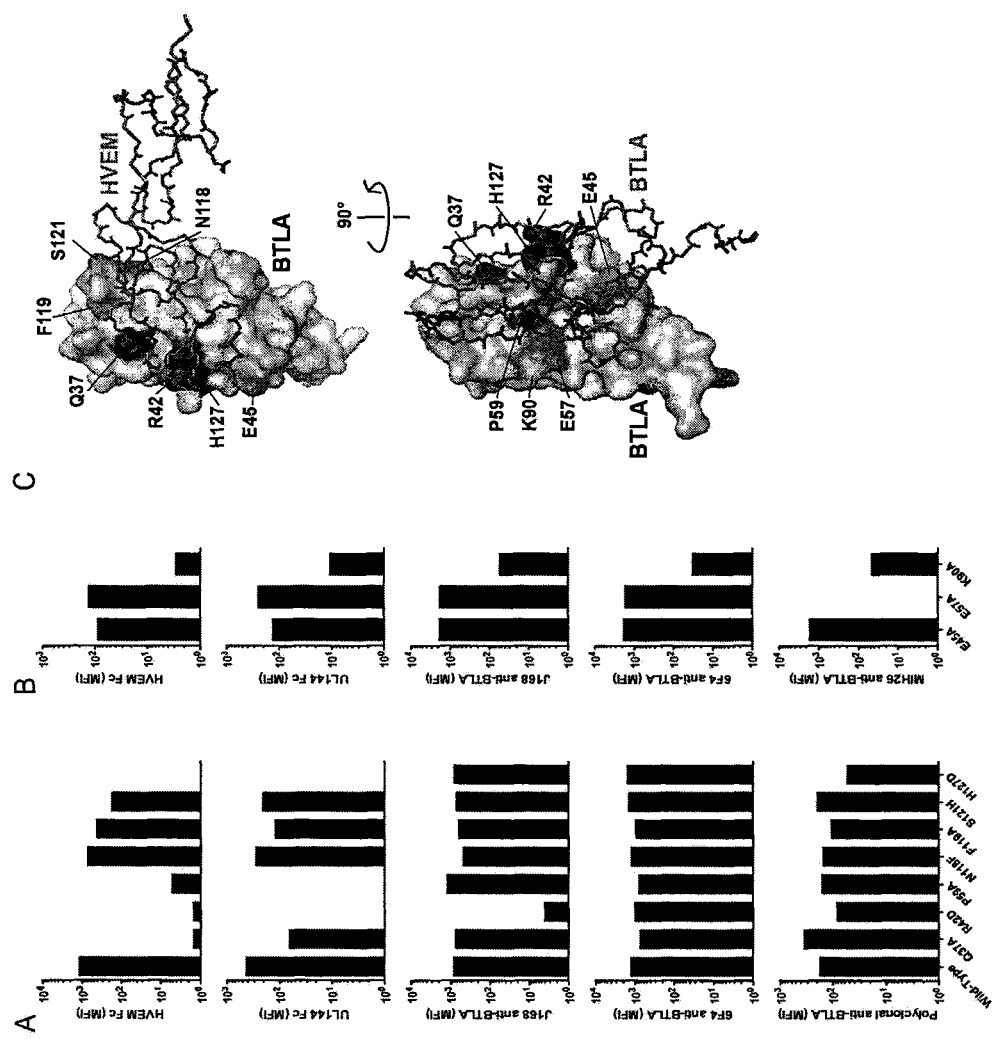
FIGS. 2A and 2B are graphical representations depicting levels of staining of HVEM Fc, human CMV UL144, or polyclonal or monoclonal antibodies specific for human BTLA of EL4 cells transduced with wild-type or mutant human BTLA
FIG. 2C illustrates a 3-D structure of BTLA complexed to HVEM (top) and rotated 90° about the y-axis complexed with a second BTLA Ig molecule (bottom).
Figure 5:
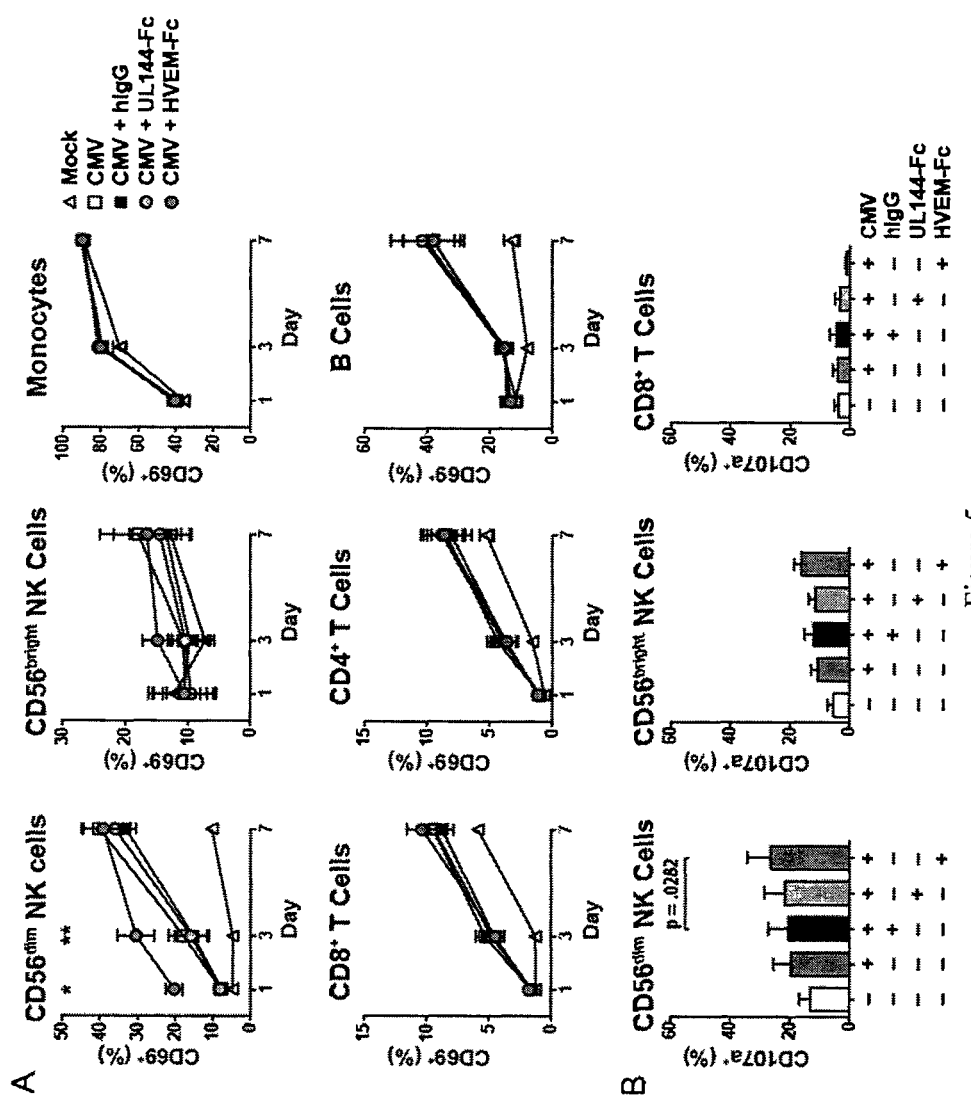
FIGS. 5A-5B are graphical representations depicting specific early co-activation of CD56dim NK cells by HVEM-Fc during response to CMV.
Figure 15:
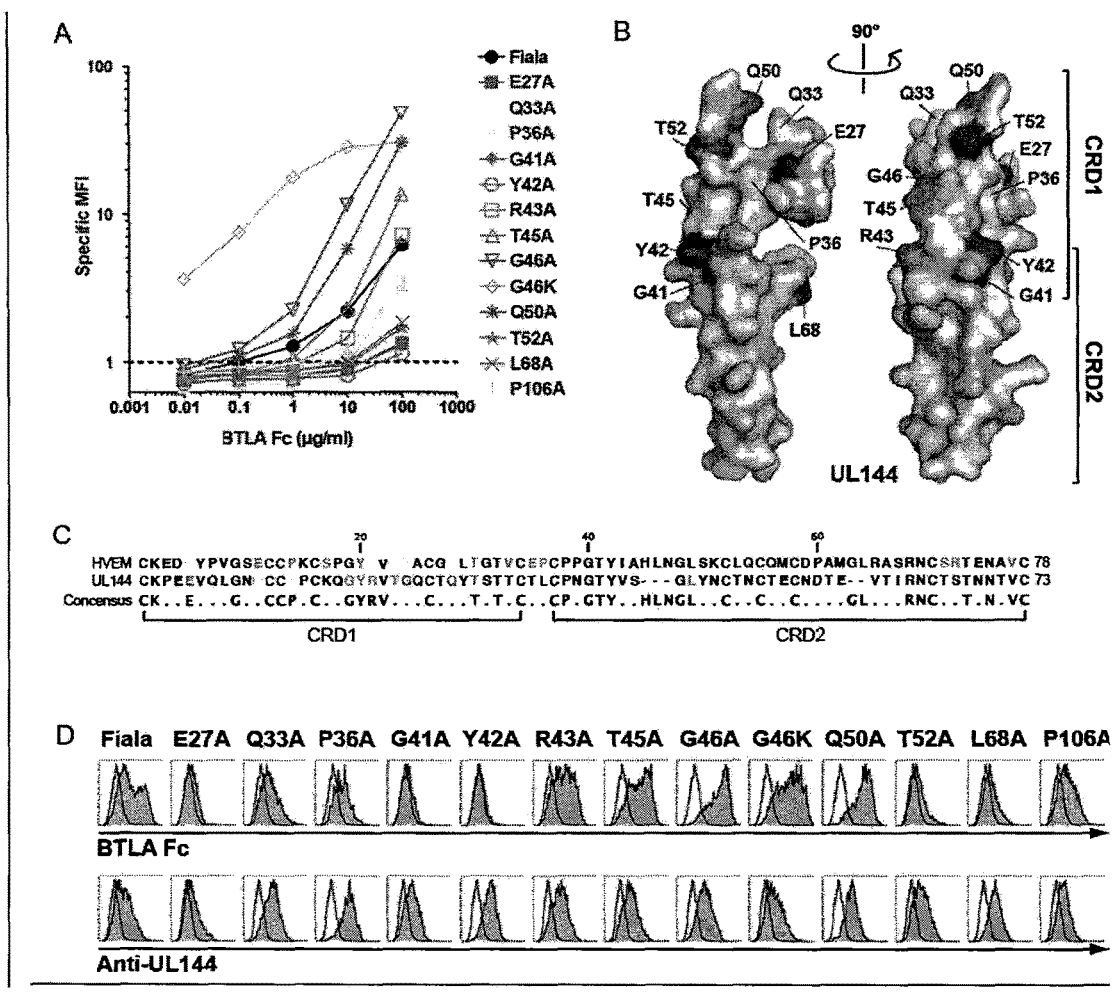
FIGS. 15A-D are a series of graphical representations related to BTLA binding to UL144 mutants.

Whether the CMV protein UL144 could bind CD160 by measuring the binding of HVEM- or UL144-Fc proteins to cells expressing human BTLA or CD160 (FIGS. 5A-B) was tested next. UL144-Fc only bound cells expressing BTLA but not CD160, while HVEM-Fc bound BTLA and CD160 with similar disassociation constants and required overlapping surfaces to bind these receptors as shown with the Y61A mutation (FIG. 5C). Whether the loss of interaction between UL144 and CD160 was due to a reduced affinity using a UL144 mutant (G46K) identified while mapping the binding surface of UL144 that bound BTLA with higher affinity (FIG. 5) was also sought to be determined. However, CD160 again failed to show any binding (FIG. 5D), although BTLA showed robust binding to the UL144 G46K mutant. The ectodomain of UL144 is highly polymorphic across different strains of human CMV with five distinct isoforms diverging up to 36% in their amino acid sequence (Table 3). UL144 selectivity for BTLA was examined throughout these diverse sequences using representative UL144 variants derived from clinical human CMV strains (FIG. 5E). Despite the extensive sequence divergence, BTLA-Fc bound all UL144 variants, whereas CD160-Fc uniformly failed to bind any of the UL144 variants. However one exception was noted, UL144 from Rhesus CMV bound human and rhesus CD160 with low affinity (FIGS. 5D-F). This interaction likely represents a divergence between human and rhesus CMV since primate BTLA and CD160 are highly similar (Tables 4-5). In contrast, HVEM and UL144 showed remarkably similar affinity for BTLA, overlapping BTLA binding surfaces, and competitive binding for BTLA coexpressed in cis with HVEM (FIG. 2, FIG. 15, Tables 6-7). Together these data show the highly selective nature of UL144 that mimics HVEM binding to BTLA but not to CD160. Thus, while both BTLA and CD160 bind HVEM with similar affinity (FIG. 7A), in resting NK cells CD160 is the predominant HVEM receptor.

TABLE 3

Alignment of CRD1 and 2 from primate HVEM and CMV UL144 sequences.

| | | | UL144 | | | | | | | HVEM | |
|---|---|---|---|---|---|---|---|---|---|---|---|
| | | | HCMV | | | | | | | | |
| | | | Gr 1A | Gr 1B | Gr 1C | Gr 2 | Gr 3 | ChCMV | RhCMV | Rhesus | Human |
| UL144 | HCMV | Gr 1A | *** | 95.9 | 98.6 | 72.6 | 76.7 | 45.2 | 41.7 | 38.4 | 42.5 |
| | | Gr 1B | 4.2 | *** | 94.5 | 72.6 | 75.3 | 45.2 | 43.1 | 39.7 | 43.8 |
| | | Gr 1C | 1.4 | 5.7 | *** | 71.2 | 75.3 | 45.2 | 40.3 | 39.7 | 43.8 |
| | | Gr 2 | 34.1 | 34.1 | 36.3 | *** | 72.6 | 46.6 | 41.7 | 41.1 | 41.1 |

TABLE 3-continued

Alignment of CRD1 and 2 from primate HVEM and CMV UL144 sequences.

| | | UL144 | | | | | | | HVEM | |
|---|---|---|---|---|---|---|---|---|---|---|
| | | HCMV | | | | | | | | |
| | | Gr 1A | Gr 1B | Gr 1C | Gr 2 | Gr 3 | ChCMV | RhCMV | Rhesus | Human |
| HVEM | Gr 3 | 27.9 | 29.9 | 29.9 | 34.1 | *** | 49.3 | 41.7 | 38.4 | 43.8 |
| | ChCMV | 93.6 | 93.6 | 93.6 | 89.5 | 81.7 | *** | 43.8 | 40.5 | 48.6 |
| | RhCMV | 105.4 | 100.6 | 110.4 | 105.4 | 105.4 | 98 | *** | 52.7 | 55.4 |
| | Rhesus | 117.9 | 112.5 | 112.5 | 107.4 | 117.9 | 109.5 | 72.9 | *** | 84.6 |
| | Human | 102.6 | 98 | 98 | 107.4 | 98 | 83.5 | 66.5 | 17.3 | *** |

Percent similarity in upper triangle, percent divergence in lower triangle.

TABLE 4

Percent similarity between primate BTLA extracellular domain.

| | Human BTLA | Chimpanzee BTLA | Rhesus BTLA |
|---|---|---|---|
| Human BTLA | *** | 100 | 89 |
| Chimpanzee BTLA | *** | *** | 89 |
| Rhesus BTLA | *** | *** | *** |

TABLE 5

Percent similarity between primate CD160 extracellular domain.

| | Human CD160 | Chimpanzee C160 | Rhesus CD160 |
|---|---|---|---|
| Human CD160 | *** | 100 | 90 |
| Chimpanzee CD160 | *** | *** | 90 |
| Rhesus CD160 | *** | *** | *** |

TABLE 6

Monovalent and bivalent kinetic rate constants for Fc fusion protein binding.

| | Analyte | | |
|---|---|---|---|
| | HVEM Fc | HuCMV UL144 Fc | RhCMV UL144 Fc |
| Monovalent Analysis | | | |
| $k_a$ (×10$^4$ M$^{-1}$s$^{-1}$) | 3.74 | 1.61 | 2.28 |
| $k_d$ (×10$^{-3}$ s$^{-1}$) | 6.60 | 4.76 | 29.5 |
| $K_D$ (nM) | 177 | 295 | 1300 |
| Bivalent Analysis | | | |
| $k_{a1}$ (×10$^4$ M$^{-1}$s$^{-1}$) | 1.53 | 0.781 | 1.66 |
| $k_{d1}$ (×10$^{-3}$ s$^{-1}$) | 9.02 | 5.10 | 31.0 |
| $k_{a2}$ (×10$^{-3}$ M$^{-1}$s$^{-1}$) | 57.3 | 0.0139 | 0.0192 |
| $k_{d2}$ (s$^{-1}$) | 2.05 | 0.00289 | 0.129 |

TABLE 7

Summary of human BTLA Mutations.

| BTLA | Anti-BTLA 6F4 | Anti-BTLA J168 | Anti-BTLA MIH26 | HVEM Fc | HuCMV UL144 Fc |
|---|---|---|---|---|---|
| Wild-Type | + | + | + | + | + |
| Q37A | + | + | + | − | +/− |
| R42D | + | − | + | − | − |
| E45A | + | + | + | + | + |
| E57A | + | + | − | + | + |
| P59A | + | + | + | − | − |
| K90A | +/− | +/− | +/− | − | − |
| N118F | + | + | + | + | + |
| F119A | + | + | + | + | + |
| S121H | + | + | + | + | + |
| H127D | + | + | + | − | − |
| A117V | + | + | + | +/− | +/− |
| A117V, Q37A | + | + | + | − | − |
| A117V, L38H | + | + | + | − | − |
| A117V, R42D | + | − | + | − | − |
| A117V, P59A | + | + | + | − | − |
| A117V, H127D | + | + | + | − | − |
| A117V, S128H | + | + | + | − | − |

TABLE 8

Summary of human HVEM Mutations.

| HVEM | Anti-HVEM | LIGHT-FLAG | BTLA-Fc | CD160-Fc |
|---|---|---|---|---|
| Wild-Type | + | + | + | + |
| P59S | n.d. | + | + | − |
| G60D | + | − | − | − |
| Y61C | + | + | − | − |
| G72P | n.d. | + | − | − |
| T82P | n.d. | − | − | − |
| R109W | + | + | + | − |
| G232S | n.d. | + | + | + | n.d.—not done.

HVEM-Fc Co-Stimulates Cytokine Activation of NK Cells.

Figure 8:
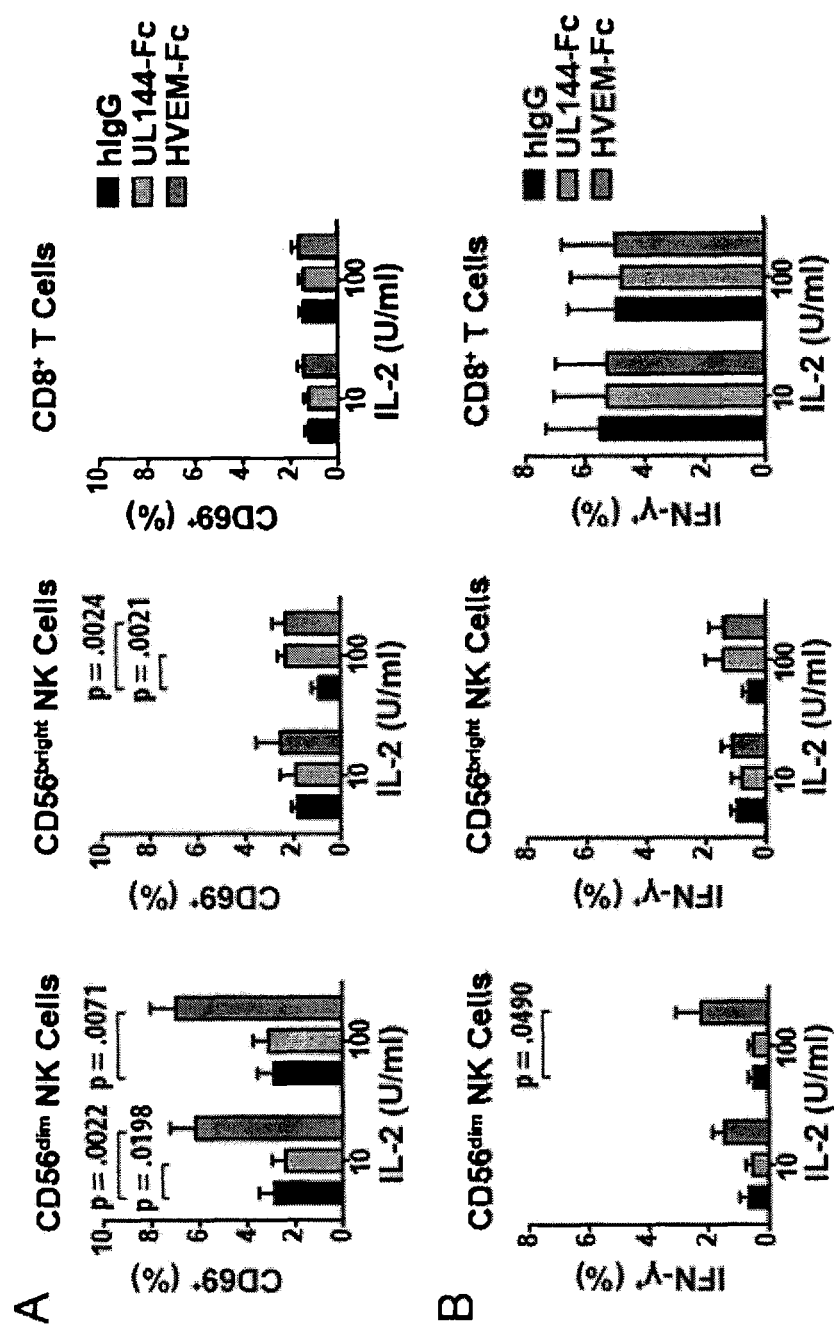
FIGS. 8A-8B are graphical representations depicting specific co-activation of CD56$^{dim}$ NK cells by HVEM-Fc in response to IL-2.
Figure 9:
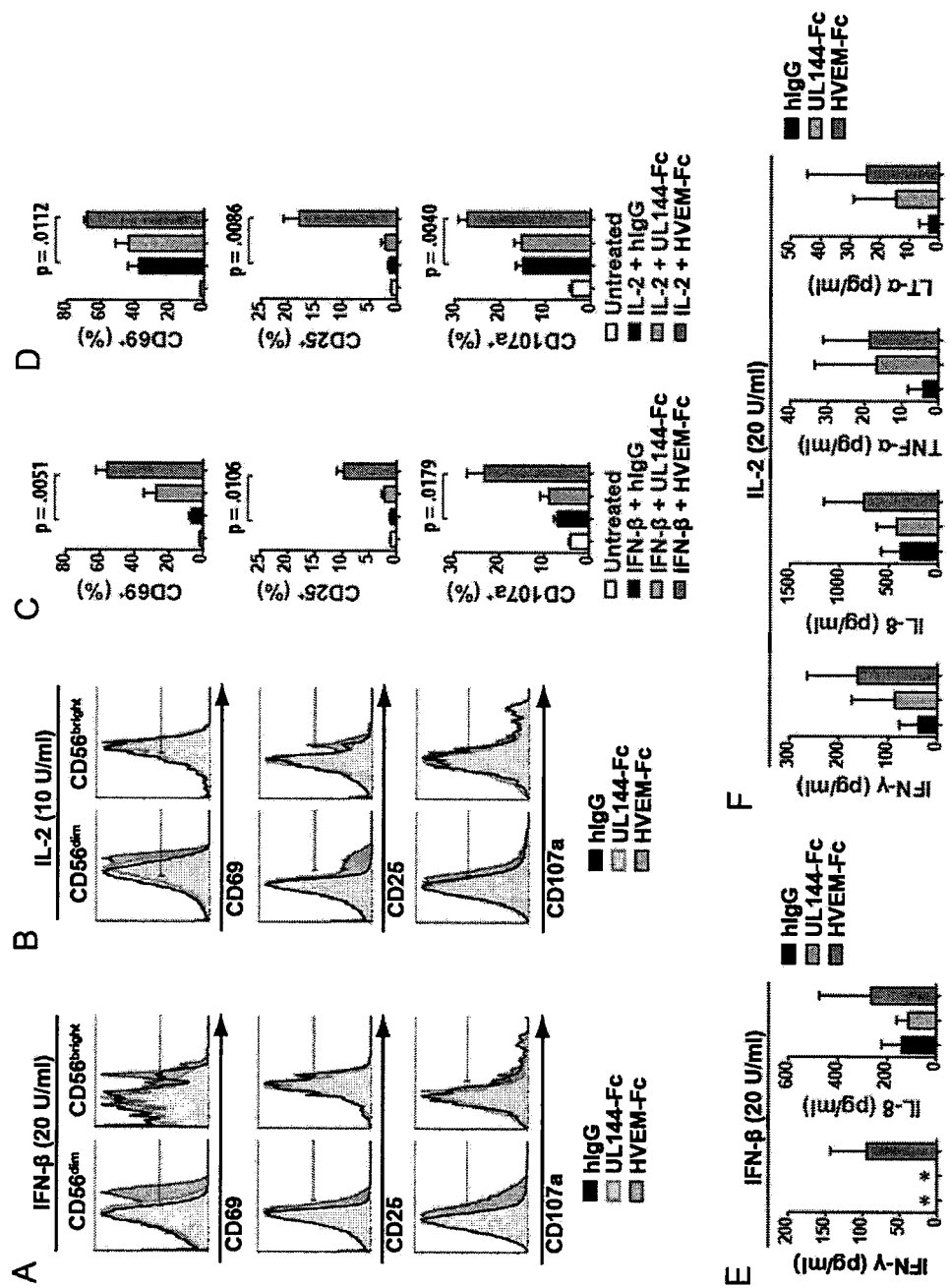
FIGS. 9A-9F are graphical representations depicting HVEM-Fc co-stimulation of IFN-β and IL-2 activation of NK cells.

Detection of virus by dendritic cells and macrophages results in early production of cytokines that prime the effector function of NK cells and help to control infection. To test how HVEM and its viral ortholog UL144 regulate cytokine activation of NK cells IL-2-induced expression of activation markers in lymphoid cells from human peripheral blood was monitored. Notably, HVEM-Fc consistently enhanced the number of CD56$^{dim}$ NK cells expressing CD69 and IFN-γ at low and high doses of IL-2 (FIG. 8). In contrast, UL144-Fc inhibited NK cell expression of CD69 but only at low doses of IL-2. CD69 induction in CD56$^{bright}$ NK cells in response to HVEM-Fc or UL144-Fc was statistically significant although the magnitude of CD69 or IFN-γ induction in CD56$^{bright}$ or cytotoxic CD8$^+$ T cells did not appreciably change. Similar co-stimulation of CD69, CD25 and CD107a expression in purified $CD56^{dim}$ NK cells in response to IL-2 and IFN-β treatment was observed, indicating that accessory cells were not required for the activity of HVEM-Fc in NK cells (FIGS. 9A-D). Increased levels of IFN-γ and IL-8 protein produced by HVEM-Fc treated pure $CD56^+$ cells stimulated with IL-2 and IFN-β (FIGS. 9E-F) were found. Additionally increased TNF-α and LT-α production in IL-2 stimulated NK cells treated with either HVEM-Fc or UL144-Fc was observed. Thus, HVEM-Fc co-stimulation drives inflammatory cytokine production in NK cells, while UL144-Fc inhibits CD69 induction while augmenting TNF cytokine production.

BTLA Inhibits Cytokine Signaling in NK Cells.

Figure 10:
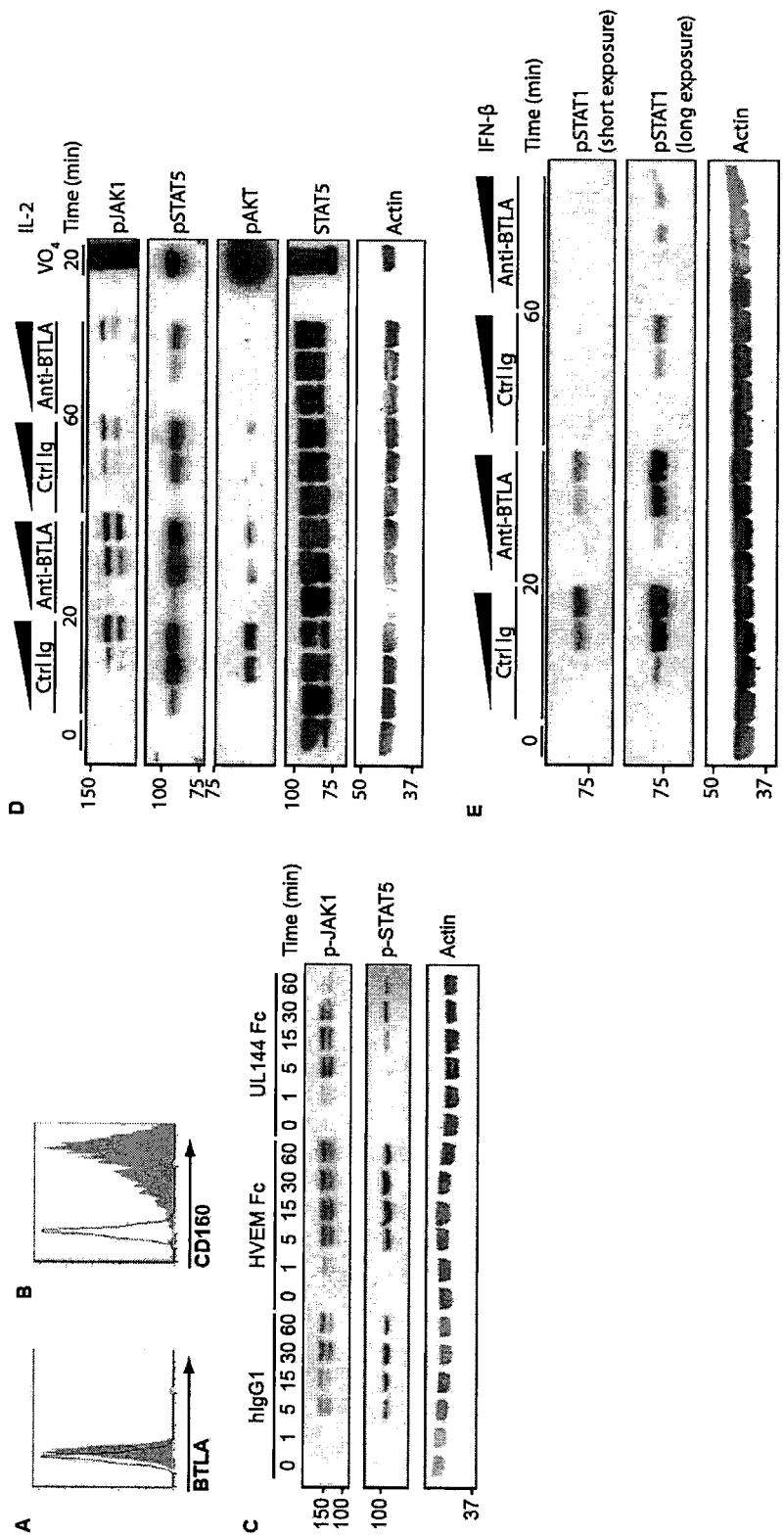
FIGS. 10A-10E are graphical and pictorial representations depicting phosphorylation of STAT1 and STAT5 is regulated by HVEM-Fc and UL144-BTLA.

The impact of HVEM-Fc or UL144-Fc on NK cell function using the NK92 cell line as a model of activated NK cells was tested next. Similar to peripheral blood NK cells, the NK92 cell line displayed abundant CD160 and low BTLA levels (FIGS. 10A-B). Human NK92 cells respond to IL-2 by phosphorylation of the kinase JAK1 leading to the activation of STAT5 (FIG. 10C). In this regard, IL-2 receptor stimulation signals rapid JAK1 and STAT5 phosphorylation peaking at 30 minutes followed by a decrease in activation through 60 minutes. Enhanced phosphorylation of both JAK1 and STAT5 following HVEM-Fc treatment, and decreased phosphorylation of JAK1 and STAT5 following UL144-Fc treatment of NK92 cells, indicating that HVEM and UL144 ligation targets IL-2 activation proximal to receptor activation was observed. Reduced IL-2-induced phosphorylation of JAK1 and STAT5, and of the downstream kinase AKT using an agonistic anti-BTLA antibody (MIH126) was observed, demonstrating that the inhibitory effect of UL144-Fc was through BTLA (FIG. 10D). Additionally, reduced IFN-β-induced STAT1 phosphorylation following anti-BTLA treatment (FIG. 10E) was observed. Thus, BTLA regulates early signaling events proximal to IL-2 and IFN-β receptor activation.

HVEM and UL144 Regulate NK Activation by Target Cells.

Figure 11:
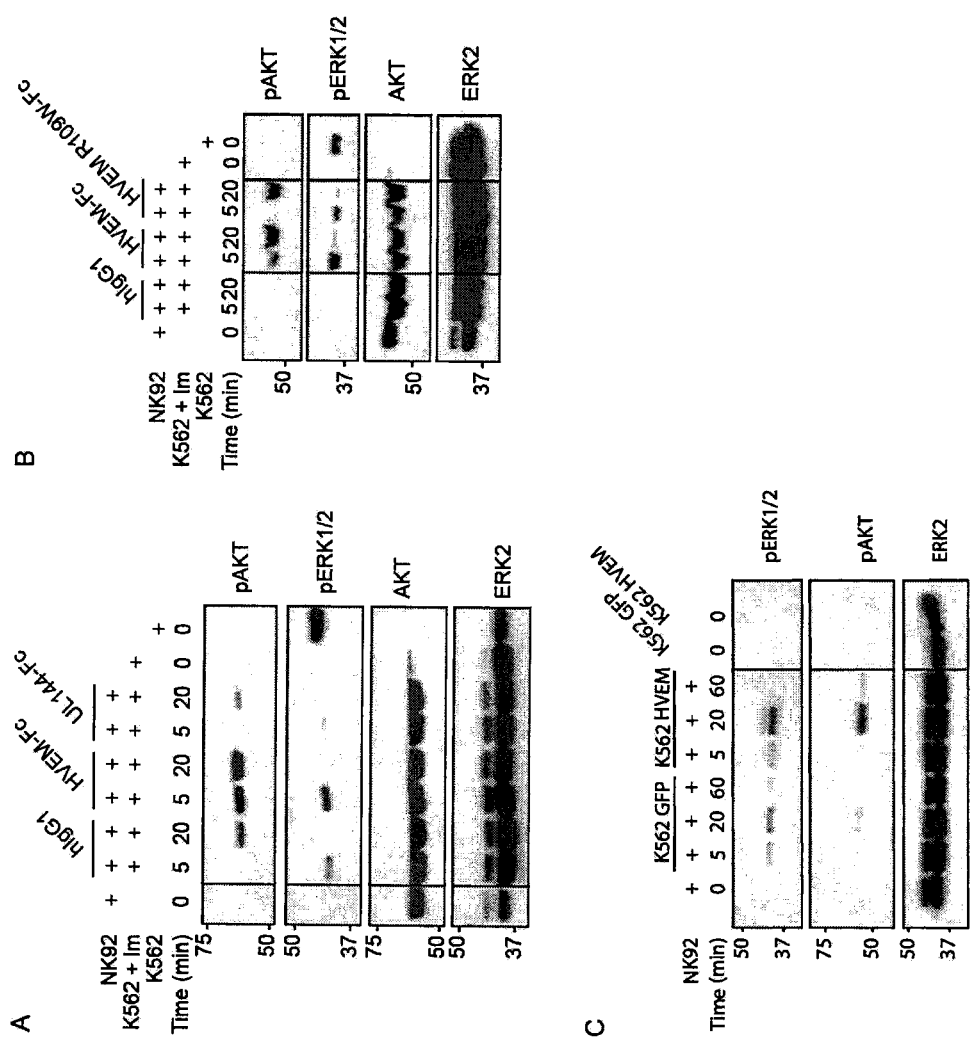
FIG. 11A-11C are pictorial representations depicting target cell activation of NK cells is regulated by HVEM and UL144.
Figure 13:
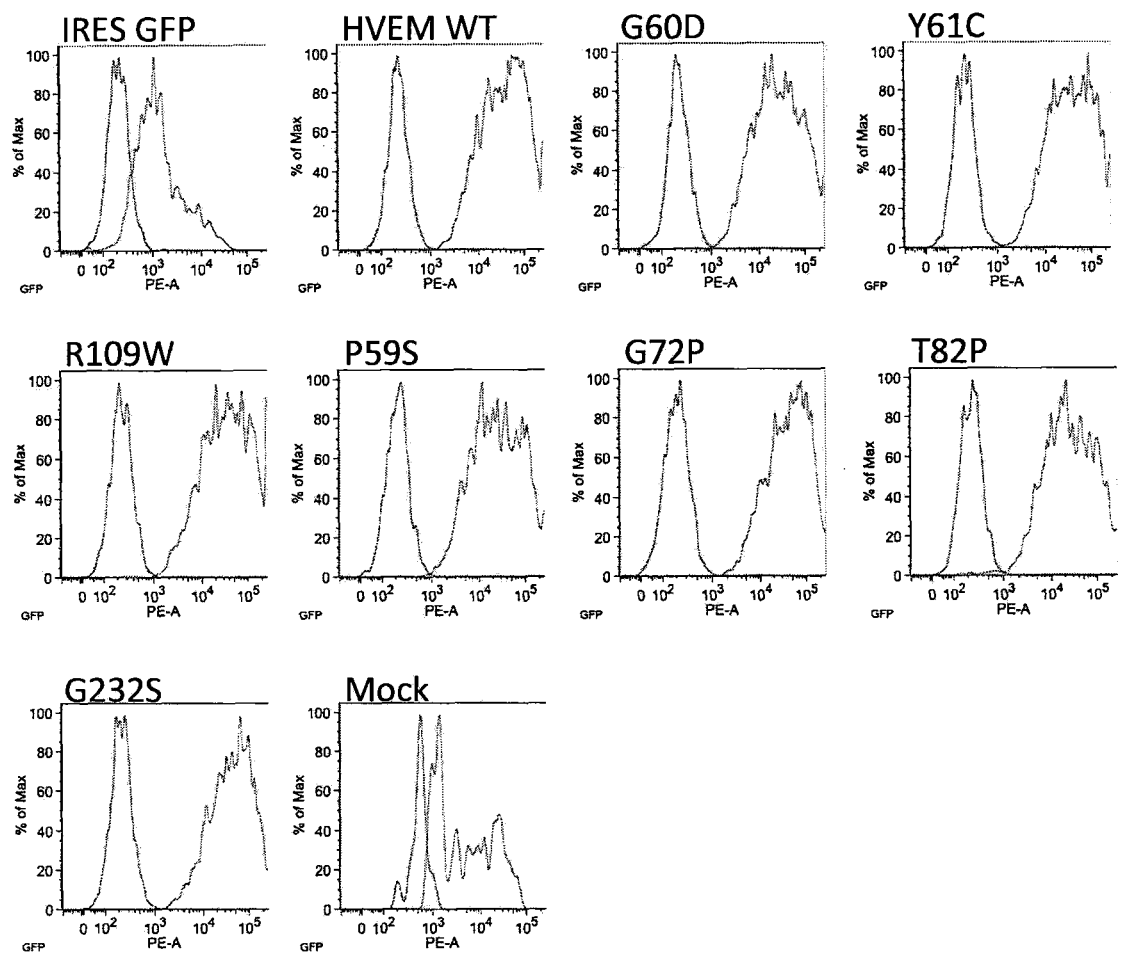
FIG. 13 is a series of graphical representations depicting expression of HVEM mutants is similar by antibody staining.
Figure 14:
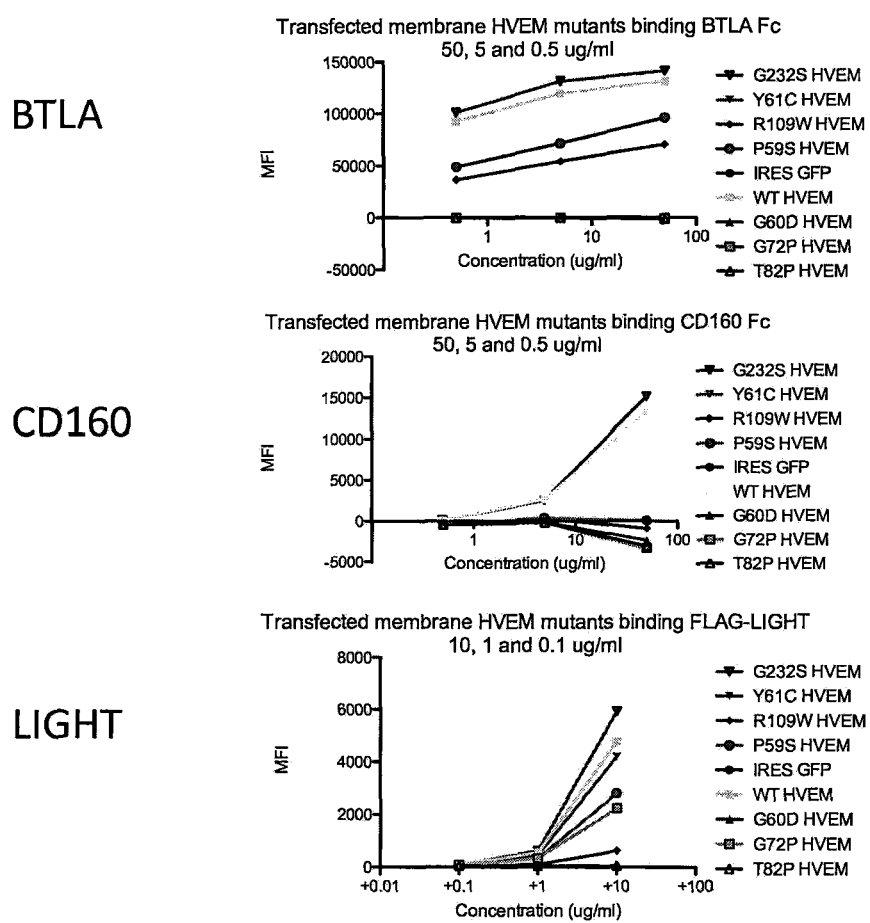
FIG. 14 is a series of graphical representations depicting comparison of LIGHT/CD160/BTLA binding to HVEM mutants.

Whether HVEM- or UL144-Fc could regulate activation of the NK92 cell line by the K562 erythroleukemia cell line was tested next. Co-culture of NK92 cells with K562 cells results in rapid ERK phosphorylation at 5 minutes and AKT phosphorylation at 20 minutes (FIG. 11A). HVEM-Fc treatment of the NK92 cells co-stimulated enhanced and sustained ERK phosphorylation at 5 and 20 minutes and more rapid and robust AKT phosphorylation at 5 and 20 minutes. In contrast, UL144-Fc treatment of the NK92 cells quenched ERK and AKT phosphorylation. When NK92 cells were treated with a mutant HVEM-Fc which ablates CD160 binding prior to co-culturing with K562 cells, this mutant was found to co-stimulate reduced AKT and ERK phosphorylation as compared to the wild-type HVEM-Fc (FIG. 1B). Whether co-stimulation of NK92 cells involved Fc receptor binding using K562 cells transduced with HVEM or control vector was tested next. NK92 cells co-cultured with HVEM-expressing K562 cells also show co-stimulated ERK and AKT phosphorylation as compared to control K562 cells (FIG. 11C). Thus, HVEM costimulates cellular activation of NK cells through CD160, while UL144 inhibits NK cell activation by target cells.

Selective HVEM Mutations Distinguish Ligand Interactions.

A recent report has identified mutations in TNFRSF14 as a frequent alteration in follicular B cell lymphoma. While many of the alterations result in nonfunctional proteins, several appear to be produced as full length transcripts. These mutations were expressed and their interactions with HVEM ligands LIGHT, BTLA and CD160 were tested. 293 cells transfected with wild-type HVEM, G60D, Y61C, R109W mutant HVEM or control vector were stained with anti-HVEM, LIGHT-FLAG with anti-FLAG antibody, BTLA-Fc with anti-Fc, or CD160-Fc with anti-Fc. All mutants were equivalently expressed. Five of the seven (71%) mutants retained LIGHT binding with G60D and T82P being the exception. Three of the mutants retained BTLA binding (43%). Notably, only one of the mutants (G232S) (14%) retained CD160 binding. Thus, in human lymphoma in which full length HVEM is produced, HVEM interactions with CD160 are the most targeted mutation.

CD160 activates NK cell cytolysis and production of interferon-γ, TNF-α, and IL-6 by engaging HLA-C. While BTLA activation reduces CD3ζ phosphorylation in T cells and Syk, BLNK, and PLCγ2 phosphorylation in B cells, the function of BTLA in NK cells has not been established. Thus, human CMV may have evolved UL144 as a BTLA specific ligand to inhibit lymphoid cell activation, and specifically to diminish NK cell activation without triggering effector functions associated with HVEM activation.

Here, a mechanism is revealed which is used by human CMV to inhibit cytokine responsiveness in NK cells by exclusively activating BTLA without triggering CD160 activation. Unlike HVEM, which engages BTLA, CD160, LIGHT, LTα and gD of herpes simplex virus, the human CMV protein UL144 only binds BTLA. Importantly, UL144 and BTLA decreased signaling directly, as well as IL-2 responsiveness by decreasing expression of the IL-2Rα chain (CD25) leading to corresponding decrease in CD69 expression. NK cells express high levels of CD160, and therefore UL144 appears to have evolved to avoid binding to CD160 in order to specifically access BTLA. HVEM, in contrast to UL144, serves as an activating ligand for CD160, which acts dominantly in NK cells. CD160 engagement of MHC-1 can also activate NK cells. Mechanistically, UL144/BTLA signaling inhibits JAK1 activation by IL-2 and IFN-β, limiting NK cell expression of LT-β and interferon-γ, thus attenuating two significant anti-viral effector functions critical for host defense to CMV.

The coexpression of CD160 and BTLA in NK cells may determine whether HVEM binding delivers an activating or inhibitory signal. The similar affinity of HVEM for CD160 and BTLA suggests that abundant NK cell CD160 is preferentially bound to HVEM in the environment. This model of receptor accessibility suggests that most surface BTLA is unbound (free). UL144 bypasses CD160 directly accessing inhibitory signaling through BTLA, a key feature of inhibition of NK cell activation.

The results indicate that HVEM promotes NK cell activation, consistent with the idea that CD160 is an activating receptor. Recent work has demonstrated the presence of an alternative splice variant of CD160 containing a cytoplasmic tail and activating motifs (ITAM). It was determined that the majority (~80%) of CD160 is GPI-linked, while the phospholipase uncleavable fraction most likely represents transmembrane CD160, however this feature remains to be established. CD160 was also shown to act as an inhibitory receptor in a fraction of $CD4^+$ T cells notably lacking the transmembrane variant, however it remains unclear how GPI-linked proteins initiate inhibitory signaling. UL144-BTLA inhibition of JAK1 phosphorylation is consistent with activation and recruitment of BTLA-SHP1 to the IL-2 receptor-β chain resulting in its dephosphorylation. UL144/BTLA facilitates the capacity of SHP1 to inhibit IL2Rb2 signaling. It remains to be determined whether the specific target of BTLA is JAK1 or the IL-2 receptor itself. Interestingly SHP1 has been linked to several JAK1-activating cytokine pathways including IL-4, IL-13 and type I interferon, and it is possible that through UL144 CMV broadly affects cytokine activation in a similar manner to those of other viral proteins.

Common γ chain signaling is absolutely required for NK cell development, maturation, and possibly memory formation primarily in response to IL-15. It may be that the role of UL144 during infection is to attenuate these homeostatic signals, thus decreasing the frequency of CMV-specific NK cells and increasing the number of surviving infected cells able to produce infectious virus. Interestingly, deregulation of IL-2 signaling in the absence of BTLA was proposed as a possible mechanism for increased homeostatic expansion of BTLA-deficient CD8$^+$ T cells. The results that CMV-UL144 blocks interferon-γ expression shows how CMV can circumvent IL-2 stimulated interferon IFNγ in NK cells. Moreover, the UL144 inhibition of LTαβ in NK cells may impact the production of IFNαβ in virus-infected stromal cells. Therefore in addition to broadly dampening activating signals CMV-UL144 may regulate anti-viral cytokine production to promote viral replication and spread.

The uniform BTLA selectivity among all UL144 variants implies it has a particularly forgiving structure, however, the factors that drive hypervariability of the UL144 ectodomain remain elusive. BTLA-expressing T cells can be inhibited by HVEM expressed by antigen presenting cells, regulatory T cells, or in mucosal epithelium. In contrast, CD160 activation by MHC class I molecules contributes to T cell costimulation and increased NK cell cytotoxicity and cytokine production mediated by enhanced Syk, AKT, and ERK activation. Interestingly, it was found that within follicular lymphoma the most common secondary karyotypic alteration at 1p36 is due to deletions or mutations in TNFRSF14, and that patients with these additional changes are associated with worse prognosis. In accordance with the cancer immunoediting model HVEM-expressing tumors may be eliminated by NK or CD8$^+$ T cells through CD160-HVEM interactions while HVEM-deficient tumors may escape immunosurveillance and progress to acquire additional mutations resulting in poor clinical outcome. The association between different strains of CMV and disease outcome in congenital or postnatal infection is controversial. Nevertheless, there continue to be reports that specific CMV variants encoding unique UL144 sequences may be associated with termination of pregnancy, or in newborns viremia, symptomatic infection and developmental sequelae. Thus, regulation of HVEM-BTLA-CD160 may represent a common mechanism of immune evasion by pathogens, which by extension is a potential target for therapeutic manipulation to control inflammatory responses.

The previous results demonstrate that BTLA inhibitory signaling predominates using an HVEM mutein that avoids CD160. These results predict that that antagonists of HVEM binding to CD160 in cis or trans on NK cells and other effector cells such as memory T cells will also promote the inhibitory action of HVEM to suppress inflammation. Specific antagonists would include monovalent fragments of antibodies, and other protein based inhibitors. These antagonists would be selected by assays which utilize disruption of the HVEM CD160 interaction resulting in inhibition of effector cell activation as measured by cytolysis, cytokine expression or changes in other markers of inflammatory action such as CD69, CD25, LTαβ, and interferon regulated genes.

Example 2

Treatment of Crohn's Disease Using HVEM Variants

Dysregulation of the immune system contributes to the pathogenesis of inflammatory bowel diseases (IBD) including Crohn's Disease and ulcerative colitis. In these diseases, hyper-activated T cells and innate lymphoid cells mediate tissue destructive processes in mucosal tissues. The TNF superfamily of cytokines and their cognate receptors have emerged as clinically relevant targets in IBD. The TNF receptor, herpesvirus entry mediator (HVEM; TNFRSF14) is unique in this superfamily because it activates both inflammatory and inhibitory signaling, mediating immune system homeostasis. It has been demonstrated that specifically targeting the inhibitory ligand of HVEM, B and T lymphocyte attenuator (BTLA) with protein-based therapeutics suppresses intestinal inflammation. Specific HVEM polypeptide variants targeting BTLA that attenuates persistent immune and inflammatory processes and reestablishes immunologic homeostasis are envisioned. The proof of mechanism study will target patients with Crohn's disease and ulcerative colitis. IBD patients refractory to steroid and TNF inhibitors therapy is a significant unmet medical need. The treatment goal is to induce clinical remission in these IBD patients by targeting the HVEM-BTLA pathway to restore immune homeostasis.

Crohn's disease and ulcerative colitis are two idiopathic relapsing inflammatory bowel disorders. Ulcerative colitis is a non-transmural inflammatory disease that is restricted to the colon, whereas Crohn's disease is a transmural inflammatory disease of the mucosa that may affect discontinuous regions along the entire gastrointestinal tract from the mouth to the anus with complications including strictures, abscesses, or fistulas. The chronic inflammatory disorder is frequently associated with disease complications and extraintestinal conditions. The annual incidence of hospitalizations in Crohn's disease is 20%. Half of the patients require surgery within 10 years after diagnosis and the risk of postoperative recurrence is 44-55% after 10 years.

Current treatment regimes involve progressive dosing with 5-aminosalicylic acid compounds, corticosteroids, TNF inhibitors, and eventually surgical intervention. Induction of remission is the main therapeutic goal followed with a shift to maintenance dosing. Although TNF antagonists are used in treating Crohn's disease and ulcerative colitis, the lack and/or loss of therapeutic responses in a substantial portion of patients remains a clinical challenge. Recently there have been advances in the understanding of the pathophysiology of IBD including both dysregulated activation of the acquired immune system, as well as innate immune system and intestinal epithelium involvement. These advances have opened new opportunities to control IBD. The therapeutic paradigm is shifting beyond simple immunosuppression to the reinforcement of the intestinal barrier. New agents that target inflammatory pathways are therefore needed.

New evidence indicates that specifically targeting the HVEM-BTLA pathway will impact both T cell and innate inflammatory cells in a physiological fashion that reflects the natural protective mechanisms of mucosal epithelia cells.

The HVEM polypeptide variants will specifically target the HVEM-BTLA pathway to attenuate inflammatory pathways and pathologic immune responses.

HVEM (TNFRSF14) is a key component of the cytokine network that includes TNF, Lymphotoxin (LT)-α, LTβ, and LIGHT (TNFSF14) and their cognate receptors TNFR1, TNFR2, and LTβR. This network regulates innate and adaptive inflammatory responses. HVEM is unique in the TNF Receptor family because it binds ligands in the TNF family and the Ig superfamily. HVEM binds LIGHT and LTα, and two co-receptors in the Ig superfamily, B and T lymphocyte attenuator (BTLA) and CD160. Recent evidence indicates that signals generated by HVEM depend on the context of its ligands expressed in trans or in cis.

HVEM-BTLA Expression. BTLA expression is restricted to the hematopoietic compartment. HVEM is coexpressed with BTLA in hematopoietic cells but is also detected in mucosal epithelia and endothelial cells. In contrast, CD160 is also coexpressed with HVEM and BTLA but is prominently expressed in NK cells, NKT cells, and subsets of memory CD8 T cells, intestinal intraepithelial T cells and mast cells, whereas naïve T cells and B cells do not express CD160. BTLA is uniquely engaged by HVEM as indicated by the lack of staining of BTLA-Fc in HVEM−/− mice. Thus, the proposed modified HVEM-Fc will only engage a single ligand, BTLA, which should exclusively drive inhibitory signaling.

The HVEM-BTLA Inhibitory Pathway. HVEM functions as a switch between proinflammatory (LIGHT-HVEM) and inhibitory signaling (HVEM-BTLA). A growing number of studies revealed targeting BTLA alters T and B cell immune responses, and the results herein demonstrate BTLA inhibits innate lymphocyte responses, e.g., NK cells by altering IL-2-related cytokine signaling, thus suppressing nonspecific inflammation.

HVEM-Fc Polypeptide Variant.

A specific BTLA-targeted polypeptide is to be developed, an engineered form of the human HVEM extracellular domain fused to a human IgG hinge and Fc domain. The receptor domain of the HVEM-Fc fusion will be engineered to remove LIGHT, LTα and CD160 binding activities, retaining specificity for BTLA and thus uniquely retain its anti-inflammatory signaling action. This molecule hereafter referred to as HVEM-Fc mutein HVEM-Fc polypeptide variant.

HVEM-Fc Mutein. The variant will contain a truncated form of the ~164 amino acid HVEM extracellular domain containing the first two cysteine-rich domains (CRDs). HVEM-Fc mutein will have binding activity for human BTLA through its CRD1 region, and will contain one or more mutations in CRD1 ablating binding to CD160. The Fc portion of the biologic will be a C-terminal human IgG1 effectorless Fc domain. Key residues in HVEM that separate BTLA and CD160 binding have been identified.

Engineering of HVEM-Fc Mutein.

The HVEM variant, although based on HVEM, will be deficient in LIGHT, LTα and CD160 binding. Removal of CRD4 and most or all of CRD3 will ablate binding of the first two ligands. BTLA binding is known to be mediated by CRD1. For these reasons, two Fc fusion constructs are proposed as starting points for the engineering of the BTLA-specific HVEM agonist, the first containing the first two CRDs (HVEM (39-120 with reference to SEQ ID NO: 79)), and the second containing CRD1, 2 and half of CRD3 (HVEM (39-141 with reference to SEQ ID NO: 79). Both will be expressed and purified for assessment of their binding properties for BTLA, CD160, LIGHT and LTα as well as their physicochemical characteristics. Neither construct is expected to bind to LIGHT or LTα. One of the two molecules will then be selected for engineering to remove CD160 binding while maintaining BTLA binding. As a starting point, positions P59 and R109, which bind BTLA-Fc and not CD160-Fc in a FACS-based assay, will be assessed as sites for mutagenesis.

Although the invention has been described with reference to the above example, it will be understood that modifications and variations are encompassed within the spirit and scope of the invention. Accordingly, the invention is limited only by the following claims.

What is claimed is:

1. A vector comprising a nucleic acid molecule encoding a herpesvirus entry mediator (HVEM) polypeptide variant, wherein the variant specifically binds B and T lymphocyte attenuator (BTLA) and does not bind CD160, wherein the variant is truncated as compared to a wild-type HVEM protein, the variant comprising cysteine rich domain (CRD) 1 and CRD2 and lacking CRD4 of the wild-type HVEM protein; and wherein the variant comprises an amino acid substitution at residue position 109 from the starting methionine, the substitution being R109W.

2. The vector of claim 1, wherein the variant has at least one additional amino acid substitution.

3. The HVEM polypeptide variant of claim 1, wherein the variant comprises CDR1, CDR2 and a portion of CDR3.

4. The HVEM polypeptide variant of claim 3, wherein the variant comprises an additional amino acid substitution at residue position 59, 60, 61, 72, or 82, or any combination thereof.

5. The HVEM polypeptide variant of claim 4, wherein the variant comprises one or more of P59S, G60D, Y61C, G72P, and T82P.

6. The HVEM polypeptide variant of claim 4, wherein the variant comprises an amino acid substation at residue position 59.

7. The vector of claim 1, wherein the variant consists of a R109W substitution.

8. The HVEM polypeptide variant of claim 1, wherein the variant comprises CDR1 or a portion thereof.

9. The HVEM polypeptide variant of claim 8, wherein the variant comprises an amino acid substitution at residue position 59, 60, 61, 72 or any combination thereof.

10. The HVEM polypeptide variant of claim 9, wherein the variant comprises one or more of P59S, G60D, Y61C and G72P.

11. The HVEM polypeptide variant of claim 10, wherein the variant comprises an amino acid substation at residue position 59.

12. The vector of claim 1, wherein the variant further comprises a dimerizing domain.

13. The vector of claim 12, wherein the dimerizing domain is an antibody Fc domain.

14. The vector of claim 13, wherein the Fc domain is an immunoglobulin (Ig) Fc domain.

15. The vector of claim 14, wherein the Ig Fc domain is an IgA, IgD, IgE, IgG, or IgM Fc domain.

16. The vector of claim 15, wherein the Ig Fc domain is an IgG1 Fc domain.

17. The HVEM polypeptide variant of claim 2, wherein the variant comprises amino acid residues from about 39 to 120, about 39 to 141, or about 39 to 163 of SEQ ID NO: 79.

18. A pharmaceutical composition comprising a nucleic acid molecule encoding the vector of claim 1, and a pharmaceutically acceptable carrier.

19. An isolated nucleic acid molecule encoding the vector of claim 1.

20. An expression cassette comprising the nucleic acid molecule of claim 19.

21. A vector comprising the expression cassette of claim 20.

22. An isolated host cell transformed or transfected with the nucleic acid molecule of claim 19 or the vector of claim 21.

23. A method for treating an inflammatory disease in a subject comprising administering to the subject an effective amount of a pharmaceutical composition comprising the HVEM polypeptide variant of claim 1, wherein the administering results in treatment of the inflammatory disease.

24. The method of claim 23, wherein the inflammatory disease is selected from the group consisting of rheumatoid arthritis, lupus, autoimmune diseases, Crohn's disease, ulcerative colitis, inflammatory bowel diseases, asthma, dermatitis, diverticulitis, pelvic inflammatory disease, atherosclerosis, allergies, myopathies, and leukocyte defects.

25. A method of inhibiting a proinflammatory response in a subject comprising administering to the subject an effective amount of a pharmaceutical composition comprising the HVEM polypeptide variant of claim 1, wherein the administering results in inhibition of the proinflammatory response.

26. The method of claim 25, wherein the agent inhibits activation of natural killer (NK) cells.

27. The method of claim 25, wherein the agent is a negative regulator of IL-2 signaling.

28. The method of claim 25, wherein the agent is a polypeptide.

* * * * *

UNITED STATES PATENT AND TRADEMARK OFFICE
CERTIFICATE OF CORRECTION

PATENT NO. : 9,982,023 B2  
APPLICATION NO. : 13/677703  
DATED : May 29, 2018  
INVENTOR(S) : Carl F. Ware et al.

Page 1 of 1

It is certified that error appears in the above-identified patent and that said Letters Patent is hereby corrected as shown below:

In the Specification

In Column 1, Lines 16 through 19, please replace:
"This invention was made in part with Government support under National Institutes of Health grants AI067890 and AI033068. The Government has certain rights to the invention."

With:
"This invention was made with government support under R01 AI067890 and R37 AI033068 awarded by the National Institutes of Health. The government has certain rights in the invention."

Signed and Sealed this  
Twenty-ninth Day of October, 2019

Andrei Iancu  
*Director of the United States Patent and Trademark Office*